United States Patent
Sanders et al.

(10) Patent No.: US 8,801,705 B2
(45) Date of Patent: Aug. 12, 2014

(54) ELECTROSURGICAL METHOD AND APPARATUS FOR REMOVING TISSUE WITHIN A BONE BODY

(75) Inventors: Norman R. Sanders, Hillsborough, CA (US); Darren Crawford, Los Altos, CA (US); Jean Woloszko, Austin, TX (US); David C. Hovda, Mountain View, CA (US)

(73) Assignee: ArthroCare Corporation, Austin, TX (US)

( * ) Notice: Subject to any disclaimer, the term of this patent is extended or adjusted under 35 U.S.C. 154(b) by 1066 days.

(21) Appl. No.: 12/763,630

(22) Filed: Apr. 20, 2010

(65) Prior Publication Data
US 2010/0204693 A1 Aug. 12, 2010

Related U.S. Application Data

(62) Division of application No. 10/970,796, filed on Oct. 20, 2004, now Pat. No. 7,708,733.

(60) Provisional application No. 60/512,954, filed on Oct. 20, 2003.

(51) Int. Cl.
*A61B 18/14* (2006.01)

(52) U.S. Cl.
USPC .............................. 606/41; 606/47

(58) Field of Classification Search
USPC .......................... 606/41, 45–50; 607/101–102
See application file for complete search history.

(56) References Cited

U.S. PATENT DOCUMENTS

| 2,056,377 | A | 10/1939 | Wappler | 125/303 |
| 3,633,425 | A | 1/1972 | Sanford | 73/356 |
| 3,659,607 | A | 5/1972 | Banko | 606/169 |
| 3,815,604 | A | 6/1974 | O'Malley et al. | 128/305 |

(Continued)

FOREIGN PATENT DOCUMENTS

| DE | 2946728 | 5/1981 | A61B 17/38 |
| DE | 3245570 | 6/1984 | A61B 17/38 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
(74) *Attorney, Agent, or Firm* — Matthew Scheele; Brian E. Szymczak

(57) ABSTRACT

A method for treating a bone body comprises inserting a probe having at least one active electrode into the target tissue and applying a voltage difference between an active electrode and return electrode to ablate the tissue. The method is particularly directed to removing tumors in a bone body and or removing cancellous bone in a bone body. The bone body may be a vertebral body. An apparatus includes a plurality of active electrodes and a distal section including two bends. The bends serve to prevent the active electrodes from impinging upon the shaft of an introducer needle. Also, a kit includes an electrosurgical probe, an electrosurgical generator, an introducer needle, and a fluid connector to connect the introducer needle to a fluid source such that liquid may be supplied to the target site during an application.

11 Claims, 28 Drawing Sheets

(56) References Cited

U.S. PATENT DOCUMENTS

| | | | |
|---|---|---|---|
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,161,950 A | 7/1979 | Cowan et al. | 606/48 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,269,174 A | 5/1981 | Adair | 128/842 |
| 4,326,529 A | 4/1982 | Doss et al. | 128/303 |
| 4,381,007 A | 4/1983 | Doss | 128/303 |
| 4,449,926 A | 5/1984 | Weiss | 433/32 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,214 A | 2/1986 | Nordenstrom et al. | 607/127 |
| 4,573,448 A | 3/1986 | Kambin | 606/170 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,020 A | 5/1989 | Augustine | 128/207.14 |
| 4,832,048 A | 5/1989 | Cohen | 128/786 |
| 4,896,671 A | 1/1990 | Cunningham et al. | 600/374 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,958,539 A | 9/1990 | Stasz et al. | 76/104.1 |
| 4,966,597 A | 10/1990 | Cosman | 606/50 |
| 4,967,765 A | 11/1990 | Turner et al. | 128/785 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,084,045 A | 1/1992 | Helenowski | 606/32 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,156,151 A | 10/1992 | Imran | 600/375 |
| 5,158,565 A | 10/1992 | Marcadis et al. | 606/185 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,201,729 A | 4/1993 | Hertzmann et al. | 606/2 |
| 5,207,675 A | 5/1993 | Canady | 606/40 |
| 5,207,684 A | 5/1993 | Nobles | 606/108 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,290,273 A | 3/1994 | Tan | 606/9 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,564 A | 6/1994 | Eggers | 606/47 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,336,443 A | 8/1994 | Odashima | 252/511 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,429,138 A | 7/1995 | Jamshidi | 600/566 |
| 5,433,739 A | 7/1995 | Sluijter et al. | 607/99 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,439,446 A | 8/1995 | Barry | 604/103 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,542,945 A | 8/1996 | Fritzsch | 606/48 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,571,189 A | 11/1996 | Kuslich | 623/17.12 |
| 5,584,872 A | 12/1996 | LaFontaine et al. | 607/117 |
| 5,609,151 A | 3/1997 | Mulier et al. | 128/642 |
| 5,617,854 A | 4/1997 | Munsif | 600/374 |

(56) References Cited

U.S. PATENT DOCUMENTS

| | | | |
|---|---|---|---|
| 5,618,587 A | 4/1997 | Markle et al. ............ 427/430.1 |
| 5,626,136 A | 5/1997 | Webster, Jr. ................ 600/373 |
| 5,626,576 A | 5/1997 | Janssen ...................... 606/41 |
| 5,632,761 A | 5/1997 | Smith et al. ................ 606/192 |
| 5,633,578 A | 5/1997 | Eggers et al. ............... 323/301 |
| 5,647,869 A | 7/1997 | Goble et al. ................. 606/37 |
| 5,660,836 A | 8/1997 | Knowlton .................... 424/400 |
| 5,662,680 A | 9/1997 | Desai ........................ 606/210 |
| 5,676,693 A | 10/1997 | LaFontaine et al. .......... 607/116 |
| 5,681,282 A | 10/1997 | Eggers et al. ............... 604/114 |
| 5,683,366 A | 11/1997 | Eggers et al. ............... 604/114 |
| 5,697,281 A | 12/1997 | Eggers et al. ............... 604/114 |
| 5,697,536 A | 12/1997 | Eggers et al. ............... 604/114 |
| 5,697,882 A | 12/1997 | Eggers et al. ............... 604/114 |
| 5,697,909 A | 12/1997 | Eggers et al. ............... 604/114 |
| 5,700,262 A | 12/1997 | Acosta et al. ............... 606/48 |
| 5,720,744 A | 2/1998 | Eggleston et al. ........... 606/40 |
| 5,725,524 A | 3/1998 | Mulier et al. ................ 606/41 |
| 5,762,629 A | 6/1998 | Kambin .................... 604/164.11 |
| 5,766,153 A | 6/1998 | Eggers et al. ............... 604/114 |
| 5,766,252 A | 6/1998 | Henry et al. ................ 623/17.16 |
| 5,785,705 A | 7/1998 | Baker ......................... 606/32 |
| 5,807,306 A | 9/1998 | Shapland et al. ............ 604/21 |
| 5,807,395 A | 9/1998 | Mulier et al. ................ 606/41 |
| 5,810,764 A | 9/1998 | Eggers et al. ............... 604/23 |
| 5,810,809 A | 9/1998 | Rydell ........................ 606/49 |
| 5,817,033 A | 10/1998 | Desantis et al. ............. 600/562 |
| 5,820,580 A | 10/1998 | Edwards et al. ............. 604/22 |
| 5,823,955 A | 10/1998 | Kuck et al. .................. 600/374 |
| 5,836,875 A | 11/1998 | Webster, Jr. ................ 600/374 |
| 5,843,019 A | 12/1998 | Eggers et al. ............... 604/22 |
| 5,846,196 A | 12/1998 | Siekmeyer et al. .......... 600/374 |
| 5,849,009 A | 12/1998 | Bernaz ....................... 606/36 |
| 5,860,951 A | 1/1999 | Eggers ....................... 604/510 |
| 5,860,974 A | 1/1999 | Abele ......................... 606/41 |
| 5,860,975 A | 1/1999 | Goble et al. ................. 606/45 |
| 5,871,469 A | 2/1999 | Eggers et al. ............... 604/114 |
| 5,873,855 A | 2/1999 | Eggers et al. ............... 604/114 |
| 5,877,289 A | 3/1999 | Thorpe et al. ............... 530/387.7 |
| 5,885,277 A | 3/1999 | Korth ......................... 606/35 |
| 5,888,198 A | 3/1999 | Eggers et al. ............... 604/114 |
| 5,891,095 A | 4/1999 | Eggers et al. ............... 604/114 |
| 5,891,134 A | 4/1999 | Goble et al. ................. 606/27 |
| 5,897,553 A | 4/1999 | Mulier ........................ 606/41 |
| 5,902,272 A | 5/1999 | Eggers et al. ............... 604/114 |
| 5,916,214 A | 6/1999 | Cosio et al. ................. 606/41 |
| 5,925,042 A | 7/1999 | Gough et al. ................ 606/41 |
| 5,935,083 A | 8/1999 | Williams .................... 600/561 |
| 5,941,869 A | 8/1999 | Patterson et al. ............ 604/508 |
| 5,944,715 A | 8/1999 | Goble et al. ................. 606/41 |
| 5,954,716 A | 9/1999 | Sharkey et al. .............. 606/32 |
| 5,980,504 A | 11/1999 | Sharkey et al. .............. 604/510 |
| 6,004,319 A | 12/1999 | Goble et al. ................. 606/48 |
| 6,007,570 A | 12/1999 | Sharkey et al. .............. 607/96 |
| 6,013,076 A | 1/2000 | Goble et al. ................. 606/41 |
| 6,014,584 A | 1/2000 | Hofmann et al. ............ 604/21 |
| 6,015,406 A | 1/2000 | Goble et al. ................. 606/41 |
| 6,024,733 A | 2/2000 | Eggers et al. ............... 604/500 |
| 6,027,501 A | 2/2000 | Goble et al. ................. 606/41 |
| 6,036,681 A | 3/2000 | Hooven ...................... 604/506 |
| 6,039,734 A | 3/2000 | Goble et al. ................. 606/41 |
| 6,045,532 A | 4/2000 | Eggers et al. ............... 604/114 |
| 6,047,700 A | 4/2000 | Eggers et al. ............... 128/898 |
| 6,053,172 A | 4/2000 | Hovda et al. ................ 128/898 |
| 6,056,746 A | 5/2000 | Goble et al. ................. 606/48 |
| 6,063,079 A | 5/2000 | Hovda et al. ................ 606/41 |
| 6,066,134 A | 5/2000 | Eggers et al. ............... 606/32 |
| 6,068,628 A | 5/2000 | Fanton et al. ............... 606/41 |
| 6,073,051 A | 6/2000 | Sharkey et al. .............. 607/99 |
| 6,074,386 A | 6/2000 | Goble et al. ................. 606/34 |
| 6,086,584 A | 7/2000 | Miller et al. ................. 606/41 |
| 6,090,106 A | 7/2000 | Goble et al. ................. 606/41 |
| 6,093,186 A | 7/2000 | Goble et al. ................. 606/34 |
| 6,093,187 A | 7/2000 | Lecuyer ..................... 606/45 |
| 6,095,149 A | 8/2000 | Sharkey et al. .............. 128/898 |
| 6,096,036 A | 8/2000 | Bowe et al. ................. 606/41 |
| 6,102,046 A | 8/2000 | Weinstein et al. ............ 128/898 |
| 6,105,581 A | 8/2000 | Eggers et al. ............... 128/898 |
| 6,109,268 A | 8/2000 | Thapliyal et al. ............ 128/898 |
| 6,117,109 A | 9/2000 | Eggers et al. ............... 604/114 |
| 6,122,549 A | 9/2000 | Sharkey et al. .............. 607/99 |
| 6,126,682 A | 10/2000 | Sharkey et al. .............. 607/96 |
| 6,142,992 A | 11/2000 | Cheng et al. ................ 606/34 |
| 6,146,380 A | 11/2000 | Racz et al. .................. 606/41 |
| 6,149,620 A | 11/2000 | Baker et al. ................. 604/22 |
| 6,159,194 A | 12/2000 | Eggers et al. ............... 604/500 |
| 6,159,208 A | 12/2000 | Hovda et al. ................ 606/41 |
| 6,168,593 B1 | 1/2001 | Sharkey et al. .............. 606/34 |
| 6,174,309 B1 | 1/2001 | Wrublewski et al. ......... 606/45 |
| 6,176,857 B1 | 1/2001 | Ashley ....................... 606/32 |
| 6,179,824 B1 | 1/2001 | Eggers et al. ............... 604/500 |
| 6,179,836 B1 | 1/2001 | Eggers et al. ............... 606/45 |
| 6,183,469 B1 | 2/2001 | Thapliyal et al. ............ 606/41 |
| 6,187,048 B1 | 2/2001 | Milner et al. ................ 623/17.12 |
| 6,190,381 B1 | 2/2001 | Olsen et al. ................. 606/32 |
| 6,203,542 B1 | 3/2001 | Ellsberry et al. ............. 606/41 |
| 6,210,402 B1 | 4/2001 | Olsen et al. ................. 606/32 |
| 6,214,001 B1 | 4/2001 | Casscells et al. ............ 606/41 |
| 6,224,592 B1 | 5/2001 | Eggers et al. ............... 606/32 |
| 6,228,078 B1 | 5/2001 | Eggers ....................... 606/32 |
| 6,228,081 B1 | 5/2001 | Goble et al. ................. 606/34 |
| 6,235,020 B1 | 5/2001 | Cheng et al. ................ 606/34 |
| 6,237,604 B1 | 5/2001 | Burnside et al. ............. 128/897 |
| 6,238,391 B1 * | 5/2001 | Olsen et al. ................. 606/41 |
| 6,245,107 B1 | 6/2001 | Ferree ........................ 606/61 |
| 6,254,600 B1 | 7/2001 | Willink et al. ............... 606/41 |
| 6,258,086 B1 | 7/2001 | Ashley et al. ................ 606/41 |
| 6,261,286 B1 | 7/2001 | Goble et al. ................. 606/34 |
| 6,261,311 B1 | 7/2001 | Sharkey et al. .............. 607/96 |
| 6,264,650 B1 | 7/2001 | Hovda et al. ................ 606/32 |
| 6,264,651 B1 | 7/2001 | Underwood et al. ......... 606/32 |
| 6,264,652 B1 | 7/2001 | Eggers et al. ............... 606/41 |
| 6,270,460 B1 | 8/2001 | McCartan et al. ........... 600/459 |
| 6,273,861 B1 | 8/2001 | Bates et al. ................. 600/567 |
| 6,277,112 B1 | 8/2001 | Underwood et al. ......... 606/32 |
| 6,280,441 B1 | 8/2001 | Ryan .......................... 606/45 |
| 6,283,961 B1 | 9/2001 | Underwood et al. ......... 606/41 |
| 6,293,942 B1 | 9/2001 | Goble et al. ................. 606/38 |
| 6,296,636 B1 | 10/2001 | Cheng et al. ................ 606/32 |
| 6,296,638 B1 | 10/2001 | Davison et al. ............. 606/41 |
| 6,306,134 B1 | 10/2001 | Goble et al. ................. 606/42 |
| 6,308,089 B1 | 10/2001 | von der Ruhr et al. ....... 600/338 |
| 6,309,387 B1 | 10/2001 | Eggers et al. ............... 606/41 |
| 6,312,408 B1 | 11/2001 | Eggers et al. ............... 604/114 |
| 6,319,250 B1 | 11/2001 | Falwell et al. ............... 606/41 |
| 6,322,549 B1 | 11/2001 | Eggers et al. ............... 604/500 |
| 6,330,478 B1 | 12/2001 | Lee et al. .................... 607/101 |
| 6,355,032 B1 | 3/2002 | Hovda et al. ................ 606/32 |
| 6,363,937 B1 | 4/2002 | Hovda et al. ................ 128/898 |
| 6,364,877 B1 | 4/2002 | Goble et al. ................. 606/34 |
| 6,379,350 B1 | 4/2002 | Sharkey et al. .............. 606/41 |
| 6,379,351 B1 | 4/2002 | Thapliyal et al. ............ 606/41 |
| 6,391,025 B1 | 5/2002 | Weinstein et al. ........... 606/41 |
| 6,402,740 B1 | 6/2002 | Ellis et al. ................... 606/28 |
| 6,416,507 B1 | 7/2002 | Eggers et al. ............... 606/32 |
| 6,416,508 B1 | 7/2002 | Eggers et al. ............... 606/32 |
| 6,416,509 B1 | 7/2002 | Goble et al. ................. 606/37 |
| 6,428,576 B1 | 8/2002 | Haldimann ................. 623/17.16 |
| 6,432,103 B1 | 8/2002 | Ellsberry et al. ............. 606/41 |
| 6,443,988 B2 | 9/2002 | Felt et al. .................... 623/17.12 |
| 6,461,357 B1 | 10/2002 | Sharkey et al. .............. 606/45 |
| 6,464,695 B2 | 10/2002 | Hovda et al. ................ 606/32 |
| 6,468,270 B1 | 10/2002 | Hovda et al. ................ 606/32 |
| 6,468,274 B1 | 10/2002 | Alleyne et al. .............. 606/32 |
| 6,468,275 B1 | 10/2002 | Wampler et al. ............ 606/48 |
| 6,482,201 B1 | 11/2002 | Olsen et al. ................. 606/41 |
| 6,497,704 B2 | 12/2002 | Ein-Gal ...................... 606/41 |
| 6,500,173 B2 | 12/2002 | Underwood et al. ......... 606/32 |
| 6,508,839 B1 | 1/2003 | Lambrecht et al. .......... 623/17.16 |
| 6,517,498 B1 | 2/2003 | Burbank et al. ............. 600/564 |
| 6,530,922 B2 | 3/2003 | Cosman ..................... 606/34 |
| 6,540,741 B1 | 4/2003 | Underwood et al. ......... 606/32 |
| 6,558,390 B2 | 5/2003 | Cragg ........................ 606/80 |
| 6,562,033 B2 | 5/2003 | Shah et al. .................. 606/41 |

(56) References Cited

U.S. PATENT DOCUMENTS

| | | | |
|---|---|---|---|
| 6,575,968 B1 | 6/2003 | Eggers et al. | 606/41 |
| 6,578,579 B2 | 6/2003 | Burnside | 128/897 |
| 6,589,237 B2 | 7/2003 | Woloszko et al. | 606/41 |
| 6,602,248 B1 * | 8/2003 | Sharps et al. | 606/32 |
| 6,604,003 B2 | 8/2003 | Fredricks et al. | 607/99 |
| 6,611,793 B1 | 8/2003 | Burnside et al. | 2/183 |
| 6,620,155 B2 | 9/2003 | Underwood et al. | 606/32 |
| 6,620,156 B1 | 9/2003 | Garito et al. | 606/50 |
| 6,622,731 B2 | 9/2003 | Daniel et al. | 128/898 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,635,087 B2 | 10/2003 | Angelucci et al. | 623/17.11 |
| 6,645,247 B2 | 11/2003 | Ferree | 623/17.11 |
| 6,679,886 B2 | 1/2004 | Weikel et al. | 606/79 |
| 6,699,244 B2 | 3/2004 | Carranza et al. | 606/41 |
| 6,712,811 B2 | 3/2004 | Underwood et al. | 606/32 |
| 6,726,684 B1 | 4/2004 | Woloszko et al. | 606/32 |
| 6,740,093 B2 | 5/2004 | Hochschuler et al. | 606/94 |
| 6,746,451 B2 | 6/2004 | Middleton et al. | 606/79 |
| 6,749,604 B1 | 6/2004 | Eggers et al. | 606/41 |
| 6,749,605 B2 | 6/2004 | Ashley et al. | 606/41 |
| 6,749,608 B2 | 6/2004 | Garito et al. | 606/45 |
| 6,758,846 B2 | 7/2004 | Goble et al. | 606/41 |
| 6,761,718 B2 | 7/2004 | Madsen | 606/50 |
| 6,770,071 B2 | 8/2004 | Woloszko et al. | 606/41 |
| 6,772,012 B2 | 8/2004 | Ricart et al. | 607/99 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,827,716 B2 | 12/2004 | Ryan et al. | 606/41 |
| 6,837,884 B2 * | 1/2005 | Woloszko | 606/32 |
| 6,837,887 B2 | 1/2005 | Woloszko et al. | 606/41 |
| 6,837,888 B2 | 1/2005 | Ciarrocca et al. | 606/41 |
| 6,878,155 B2 | 4/2005 | Sharkey et al. | 607/96 |
| 6,918,908 B2 | 7/2005 | Bonner et al. | 606/41 |
| 6,920,883 B2 | 7/2005 | Bessette et al. | 128/898 |
| 6,921,399 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,974,480 B2 | 12/2005 | Messerli et al. | 623/17.11 |
| 6,984,231 B2 | 1/2006 | Goble et al. | 606/37 |
| 6,991,631 B2 | 1/2006 | Woloszko et al. | 606/41 |
| 6,997,885 B2 | 2/2006 | Lubock et al. | 600/567 |
| 6,997,925 B2 | 2/2006 | Maguire et al. | 606/41 |
| 7,001,431 B2 | 2/2006 | Bao et al. | 623/17.12 |
| 7,004,941 B2 | 2/2006 | Tvinnereim et al. | 606/41 |
| 7,014,633 B2 | 3/2006 | Cragg | 604/500 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,104,989 B2 | 9/2006 | Skarda | 606/41 |
| 7,108,696 B2 * | 9/2006 | Daniel et al. | 606/41 |
| 7,131,969 B1 | 11/2006 | Hovda et al. | 606/45 |
| 7,169,143 B2 | 1/2007 | Eggers et al. | 606/32 |
| 7,172,591 B2 | 2/2007 | Harano et al. | 606/34 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,241,294 B2 | 7/2007 | Reschke | 606/41 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,278,972 B2 | 10/2007 | Lamoureux et al. | 600/567 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,393,351 B2 | 7/2008 | Woloszko et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,628,780 B2 | 12/2009 | Bonner et al. | 604/500 |
| 7,632,267 B2 | 12/2009 | Dahla | 606/41 |
| 7,682,368 B1 | 3/2010 | Bombard et al. | 606/142 |
| 7,691,101 B2 | 4/2010 | Davison et al. | 606/41 |
| 7,883,515 B2 | 2/2011 | Kear | 606/127 |
| 7,951,141 B2 | 5/2011 | Sharps et al. | 606/32 |
| 7,976,554 B2 | 7/2011 | Newell et al. | 606/144 |
| 8,292,887 B2 | 10/2012 | Woloszko et al. | 606/48 |
| 2002/0029036 A1 | 3/2002 | Goble et al. | 606/38 |
| 2002/0049438 A1 | 4/2002 | Sharkey et al. | 606/41 |
| 2002/0082698 A1 | 6/2002 | Parenteau et al. | 623/17.16 |
| 2002/0120337 A1 | 8/2002 | Cauthen | 623/17.16 |
| 2003/0013986 A1 | 1/2003 | Saadat | 600/549 |
| 2003/0088245 A1 | 5/2003 | Woloszko et al. | 606/41 |
| 2003/0130655 A1 | 7/2003 | Woloszko et al. | 606/45 |
| 2003/0130738 A1 | 7/2003 | Hovda et al. | 623/17.11 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0087937 A1 | 5/2004 | Eggers et al. | 606/41 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Hovda et al. | 606/41 |
| 2005/0096645 A1 | 5/2005 | Wellman et al. | 606/41 |
| 2005/0119650 A1 | 6/2005 | Sanders et al. | 424/426 |
| 2005/0251134 A1 | 11/2005 | Woloszko et al. | 606/32 |
| 2005/0261754 A1 | 11/2005 | Woloszko et al. | 606/32 |
| 2005/0267553 A1 | 12/2005 | Staunton et al. | 607/101 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0015565 A1 | 1/2008 | Davison | 606/37 |
| 2008/0243117 A1 | 10/2008 | Sharps et al. | 606/41 |
| 2009/0105543 A1 | 4/2009 | Miller et al. | 600/155 |
| 2009/0299220 A1 | 12/2009 | Field et al. | 600/567 |
| 2010/0114110 A1 | 5/2010 | Taft et al. | 600/184 |
| 2011/0112373 A1 | 5/2011 | Ainsworth et al. | 600/207 |
| 2011/0288539 A1 | 11/2011 | Woloszko et al. | 606/33 |
| 2011/0288619 A1 | 11/2011 | Pianca | 607/116 |

FOREIGN PATENT DOCUMENTS

| | | | |
|---|---|---|---|
| DE | 3530335 | 3/1987 | A61B 17/39 |
| DE | 3930451 A1 | 3/1991 | A61B 17/39 |
| DE | 9490466 | 7/1996 | A61B 17/38 |
| EP | 515 867 | 12/1992 | A61B 17/36 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 719162 B1 | 11/1997 | A61N 1/05 |

(56) References Cited

FOREIGN PATENT DOCUMENTS

| | | | |
|---|---|---|---|
| EP | 774926 B1 | 6/1999 | ............ A61B 17/39 |
| EP | 0694290 B1 | 11/2000 | ............ A61B 18/04 |
| EP | 886495 B1 | 2/2003 | ............ A61B 18/08 |
| FR | 2313949 | 1/1977 | ............ A61N 3/02 |
| GB | 2 308 979 | 7/1997 | ............ A61B 17/36 |
| GB | 2 308 980 | 7/1997 | ............ A61B 17/36 |
| GB | 2 308 981 | 7/1997 | ............ A61B 17/36 |
| GB | 2 327 350 | 1/1999 | ............ A61B 17/39 |
| GB | 2 327 351 | 1/1999 | ............ A61B 17/39 |
| GB | 2 327 352 | 1/1999 | ............ A61B 17/39 |
| JP | 57-57802 | 4/1982 | ............ A61B 1/00 |
| JP | 57-117843 | 7/1982 | ............ A61B 17/39 |
| JP | 10/504732 | 5/1998 | ............ A61B 17/56 |
| JP | 2002-503508 | 2/2002 | ............ A61B 18/12 |
| JP | 2002-541904 | 12/2002 | ............ A61B 18/12 |
| WO | 90/03152 | 4/1990 | ............ A61B 17/39 |
| WO | 90/07303 | 7/1990 | ............ A61B 17/39 |
| WO | 92/21278 | 12/1992 | ............ A61B 5/04 |
| WO | 93/13816 | 7/1993 | ............ A61B 17/36 |
| WO | 93/20747 | 10/1993 | ............ A61B 5/00 |
| WO | 94/04220 | 3/1994 | |
| WO | 94/08524 | 4/1994 | ............ A61B 17/32 |
| WO | 94/08654 | 4/1994 | ............ A61M 37/00 |
| WO | 94/14383 | 7/1994 | ............ A61B 17/36 |
| WO | 94/26228 | 11/1994 | ............ A61B 17/00 |
| WO | 95/05781 | 3/1995 | ............ A61B 17/00 |
| WO | 95/05867 | 3/1995 | ............ A61B 17/00 |
| WO | 95/09576 | 4/1995 | ............ A61B 17/39 |
| WO | 95/30373 | 11/1995 | ............ A61B 17/00 |
| WO | 95/34259 | 12/1995 | ............ A61F 5/48 |
| WO | 96/00042 | 1/1996 | ............ A61B 17/39 |
| WO | 96/07360 | 3/1996 | ............ A61B 17/00 |
| WO | 96/20652 | 7/1996 | ............ A61B 18/14 |
| WO | 96/23449 | 8/1996 | ............ A61B 17/00 |
| WO | 96/039914 | 12/1996 | ............ A61B 1/00 |
| WO | 96/41574 | 12/1996 | ............ A61B 17/00 |
| WO | 97/00070 | 1/1997 | ............ A61K 31/415 |
| WO | 97/00646 | 1/1997 | ............ A61B 17/39 |
| WO | 97/00647 | 1/1997 | ............ A61B 17/39 |
| WO | 97/23169 | 7/1997 | ............ A61B 17/39 |
| WO | 97/24073 | 7/1997 | ............ A61B 17/39 |
| WO | 97/24074 | 7/1997 | ............ A61B 17/39 |
| WO | 97/24992 | 7/1997 | ............ A61B 18/12 |
| WO | 97/24993 | 7/1997 | ............ A61B 17/39 |
| WO | 97/24994 | 7/1997 | ............ A61B 17/39 |
| WO | 97/48345 | 12/1997 | ............ A61B 17/39 |
| WO | 97/48346 | 12/1997 | ............ A61B 17/39 |
| WO | 98/00070 | 1/1998 | ............ A61B 18/14 |
| WO | 98/01087 | 1/1998 | ............ A61F 1/03 |
| WO | 98/03117 | 1/1998 | ............ A61B 17/00 |
| WO | 98/03220 | 1/1998 | ............ A61B 18/14 |
| WO | 98/07468 | 2/1998 | ............ A61N 1/40 |
| WO | 98/11944 | 3/1998 | ............ A61N 5/02 |
| WO | 98/14131 | 4/1998 | ............ A61B 18/00 |
| WO | 98/17190 | 4/1998 | ............ A61B 18/00 |
| WO | 98/27879 | 7/1998 | ............ A61B 17/36 |
| WO | 98/27880 | 7/1998 | ............ A61B 17/39 |
| WO | 99/03414 | 1/1999 | ............ A61B 18/14 |
| WO | 99/20185 | 4/1999 | ............ A61B 17/20 |
| WO | 99/42037 | 8/1999 | ............ A61B 18/14 |
| WO | 99/47058 | 9/1999 | ............ A61B 17/39 |
| WO | 99/51155 | 10/1999 | ............ A61B 17/36 |
| WO | 99/51158 | 10/1999 | ............ A61B 17/39 |
| WO | 00/01313 | 1/2000 | ............ A61B 17/39 |
| WO | 00/07507 | 2/2000 | |
| WO | 00/10475 | 3/2000 | ............ A61B 18/14 |
| WO | 00/62698 | 10/2000 | ............ A61B 18/14 |
| WO | 00/71043 | 11/2000 | ............ A61B 18/14 |
| WO | 01/26570 | 4/2001 | ............ A61B 18/14 |
| WO | 01/87154 | 5/2001 | ............ A61B 5/05 |
| WO | 01/82813 | 11/2001 | ............ A61B 18/14 |
| WO | 02/11635 | 2/2002 | ............ A61B 18/14 |
| WO | 02/36028 | 5/2002 | ............ A61B 18/12 |
| WO | 03/024506 | 3/2003 | ............ A61B 18/14 |
| WO | 03/089997 A2 | 10/2003 | |
| WO | 2004/022155 | 3/2004 | ............ A61B 18/18 |
| WO | 2005/039390 | 5/2005 | ............ A61B 18/18 |
| WO | 2005/122938 | 12/2005 | ............ A61B 18/18 |
| WO | 2005/125287 | 12/2005 | ............ A61B 18/00 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC—III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, 2$^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York. 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.

(56) References Cited

OTHER PUBLICATIONS

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the 55$^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for in Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An in Vitro and in Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
Seal et al., "Thermal Characteristics and the Lumbar Disc: Evaluation of a Novel Approach to Targeted Intradiscal Thermal Therapy", NASS-APS First Joint Meeting, Charleston SC, Apr. 1998.
AESCULAP, "Flexible endoscope", Micro, Neuro and Spine surgery, 3 pgs. no date.
PCT International Search Report for PCT/US99/03339, 1 pg, Mailed May 14, 1999.
PCT International Search Report for PCT/US99/17821, 1 pg., Mailed Oct. 19, 1999.
PCT International Search Report for PCT/US00/13706. 1 pg., Mailed Jul. 31, 2000.
PCT International Search Report for PCT/US00/28267, 1 pg., Mailed Mar. 23, 2001.
PCT International Search Report for PCT/US01/15728, 1 pg., Mailed Oct. 18, 2001.
PCT International Preliminary Examination Report for PCT/US01/15728, 4 pgs, Jan. 23, 2003.
PCT International Search Report for PCT/US02/29469, 1 pg., Mailed May 22, 2003.
PCT International Search Report for PCT/US03/27745, 1 pg., Mailed Jul. 2, 2004.
PCT International Search Report for PCT/US05/20774, 1 pg., Mailed Oct. 26, 2005.
PCT Written Opinon of the International Searching Authority for PCT/US05/20774, 4 pgs., Mailed Oct. 26, 2005.
PCT International Search Report for PCT/US04/34949, 1 pg., Mailed Mar. 28, 2006.
PCT Written Opinon of the International Searching Authority for PCT/US04/34949, 3pgs., Mailed Mar. 28, 2006.
Supplementary EP Search Report for EP97932609, 2 pgs, Dec. 19, 2000.
EPO Communication, Supplementary EP Search Report for EP99934236, 3 pgs, Mailed Oct. 9, 2001.
EPO Communication, Supplementary EP Search Report for EP01935554, 5 pgs, Mailed Feb. 27, 2006.

(56) References Cited

OTHER PUBLICATIONS

EPO Communication, Supplementary EP Search Report for EP03749423, 3 pgs, Mailed Mar. 21, 2006.
EPO Communication, Supplementary EP Search Report for EP00936062, 6 pgs, Mailed Mar. 11, 2008.
PCT International Search Report and Written Opinion for PCT/US07/63198 10 pgs, Mailed Mar. 26, 2008.
EPO Communication, Supplementary EP Search Report for EP 05760511, 5 pgs, Jan. 12, 2011.

* cited by examiner

ELECTROSURGICAL METHOD AND APPARATUS FOR REMOVING TISSUE WITHIN A BONE BODY

CROSS-REFERENCE TO RELATED APPLICATIONS

This application is a divisional of U.S. application Ser. No. 10/970,796, filed Oct. 20, 2004, now U.S. Pat. No. 7,708,733, which claims priority to 60/512,954 filed Oct. 20, 2003, both of which are hereby incorporated by reference.

BACKGROUND OF THE INVENTION

The present invention relates generally to treating diseased bone by removing tissue from within the bone and more particularly, by immediately removing neoplastic and osteoporotic tissue using a minimally invasive electrosurgical probe. The present invention is particularly well suited for the treatment of the vertebrae as well as other bone bodies such as, for example, the femur.

Vertebroplasty is a minimally invasive percutaneous approach to treat vertebral compression fractures (VCFs). VCFs may be secondary to osteoporosis or to the presence of (and treatment) of a tumor in the vertebrae (e.g., myelomas or metastatic tumors).

Vertebroplasty involves injecting a viscous solution of bone cement (e.g., poly-methylmethacrylate) into the fractured vertebral body. The cement fills the spaces between the bone fragments and serves to stabilize the vertebral body, preventing spinal collapse. The viscous solution may include a radio-opaque material to provide fluoroscopic guidance for the physician. See, for example, U.S. Pat. Nos. 6,348,055 and 6,138,190 both issued to Preissman, describing a system for delivery of implant material to a desired site. Each patent and patent application mentioned in this patent application is hereby incorporated by reference in its entirety.

A problem with vertebroplasty procedures is the small space available within the vertebral body that may be filled with the bone cement. Small spaces in the vertebral body are generally undesirable because only a small volume of stabilizing bone cement may be added to the space. In contrast, a large space may accept a large amount of bone cement, tending to increase the life of the semi-artificial bone body.

Another problem with vertebroplasty is providing a solid surface for the bone cement to adhere. Providing a solid smooth surface for the cement to adhere to is not trivial because osteoporotic bone often consists of a multitude of bone fragments in a haphazard arrangement. Accordingly, a larger smoother cavity is desirable in vertebroplasty.

A number of patents discuss creating a space or cavity in the vertebral body for certain diagnostic and therapeutic procedures such as a procedure for fixing a bone fracture. U.S. Pat. No. 4,969,888 issued to Scholten et al. describes a method for fixation of osteoporotic bone comprising drilling the osteoporotic bone to form a cavity, followed by inflating an inflatable device inserted into the cavity. Expansion of the inflatable device compacts the bone and is stated to restore the bone height. A flowable synthetic bone material is directed into the cavity and allowed to set to a hardened condition.

U.S. Pat. No. 6,440,138 issued to Reiley (the "Reiley patent") describes another device and method for creating cavities in an interior body region such as cancellous bone. According to the Reiley patent, various tools carry structures that cut cancellous bone to form the cavity. The cutting structures include filaments in the form of a loop, or brush, a blade that may be moved laterally or rotatetively or both. Also, the structure may comprise a transmitter of energy. The Reiley patent at column 8, lines 19-30, indicates that the type of energy that the transmitter propagates to remove tissue can vary. Described examples include ultrasonic energy and laser energy at a suitable tissue cutting frequency.

A number of patents describe instruments and methods for treating tumors by applying energy from a radio frequency source. See, for example, U.S. Pat. No. 6,622,731 to Daniel.

Although the above described techniques are available, each technique has associated shortcomings. For instance, drilling and compacting the osteoporotic bone fails to remove the bone fragments. The compacted fragments provide an unstable surface for the bone cement to adhere to. The bone fragments may be reabsorbed by the bone body, leaving a void which may facilitate spinal collapse.

Additionally, inserting, expanding and deflating an inflatable member requires additional time and steps. A balloon also does not remove tissue. It compacts the tissue, leaving dead tissue within the bone body. The eventual reabsorbing of tissue leaves a void in the bone body and consequently, the patient may continue to be vulnerable to spinal collapse.

Treating tumors with heat generated from RF energy can also fail to immediately remove the tissue. As the necrotic tissue is reabsorbed, a void develops in the bone body. Such voids lead to spinal collapse.

Accordingly, a fast minimally invasive procedure and apparatus for treating bone disease of an osteoportic and non-osteoporotic origin is still desired.

SUMMARY OF THE INVENTION

The present invention is a method for removing a volume of tissue within a bone body comprising: a.) inserting a distal end of an apparatus into the bone body, the apparatus comprising an elongate shaft and an active electrode at or near the distal end, the active electrode being in electrical communication with a radio frequency controller or current generator; and b.) applying a radio frequency voltage or current to the active electrode sufficient to cause the volume to be immediately removed whereby a cavity is formed within the bone body.

The apparatus may comprise at least two active electrodes. In one variation, at least one active electrode is a ball wire. The shape of the active electrode may include an equatorial cusp and an apical spike. Each of the at least two active electrodes is connected to a wire conductor that extends at least partially through the shaft. The wire conductors collectively form a wire bundle.

The apparatus may further comprise a securing member that is wrapped around the wire bundle to prevent the active electrodes from radially expanding. The apparatus may further comprise a polymeric tubular element that holds the active electrodes in close proximity to one another. The tubular element may be positioned interior to the securing member. The apparatus may also comprise a distal portion having S-curve or bend.

The method may be carried out to operate on a bone body such as a vertebral body. The volume of tissue to be removed may be cancellous bone, a tumor, or another type of tissue.

The method may also comprise the step of injecting a stabilizing material (such as bone cement) into the cavity.

The method may also comprise supplying a venous coagulant solution prior to the step of injecting. An example of a coagulant is THROMBIN-JMI®. Coagulation may then be confirmed by injecting a saline with a tracer and observing lack of venous uptake.

The method may further comprise delivering an electrically conductive fluid to the active electrode. Additionally, during the step of applying a radio frequency current in step b.), described above, a plasma may be formed around the active electrode, the plasma having sufficient energy to molecularly disassociate the tissue.

Another variation of the present invention is an apparatus for removing tissue within a bone body comprising an elongate shaft having a distal end; at least two active electrodes arranged at or near the distal end; a wire bundle having at least two wire conductors, the wire conductors extending at least partially through the shaft and connected to the at least two active electrodes in a one to one correspondence; a return electrode spaced proximal to the active electrodes; and a malleable member wrapped around a distal section of the wire bundle to prevent the active electrodes from spreading apart from one another in an application.

The malleable member may comprise a metal wire. The apparatus may further comprise a polymeric tubular member arranged concentrically with the wire bundle, the polymeric tubular member being between the wire bundle and the malleable member. The apparatus may also comprise at least two bends, each bend being between 5 and 30 degrees. Also, each of the active electrodes may have a cusp and an apical tip. In one embodiment, the active electrodes form a bouquet arrangement.

In another variation the probe is connected to a fluid connector and the fluid connector comprises a fluid ingress port configured to fluidly communicate with an electrically conductive fluid source, and a fluid egress port configured to fluidly communicate with an introducer needle assembly. The fluid connector is also adapted to axially slide along the shaft.

Another variation of the present invention is a method for treating abnormal bone comprising instantaneously creating a cavity in the bone by ablating a volume of tissue using a radio frequency energy source. The abnormal bone may be fractured, osteoporotic, neoplastic, tissue of nonosteoporotic origin, or a combination of the tissues. The step of using radio frequency energy may comprise creating a plasma to cause the volume of the bone tissue to be removed. The method may also comprise supplying an electrically conductive fluid to a target site. The method may be carried out such that the tissue is molecularly disassociated.

Another variation of the present invention is a kit comprising: an introducer needle for penetrating a vertebrae; an apparatus as recited above; a high frequency generator in electrical communication with the apparatus. The kit may further comprise a fluid valve adapted to couple to a fluid source and to a proximal end of the introducer needle, and the valve further being slideable along the shaft.

For a further understanding of the nature and advantages of the invention, reference should be made to the following description taken in conjunction with the accompanying drawings.

DESCRIPTION OF SPECIFIC EMBODIMENTS

The present invention provides systems and methods for selectively applying electrical energy to a target location within or on a patient's body, particularly including tissue within a bone body such as tumors (especially metastatic tumors), osteoporotic bone fragments, and bone fragments of nonosteoporotic origin. Examples of procedures include, but are not limited to, any procedure that may benefit from creating a void or cavity in a bone body such as a vertebroplasty procedure, channeling bone tissue, removing tumors, removing cancellous bone (in the spine, leg bones or other peripheral or non-peripheral bones), interspinous tissue, degenerative discs, laminectomy/discectomy procedures for treating herniated discs, decompressive laminectomy for stenosis in the lumbosacral and cervical spine, localized tears or fissures in the annulus, nucleotomy, disc fusion procedures, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures, or using minimally invasive techniques, such as thoracoscopy, arthroscopy, laparascopy, or percutaneous and the like.

Figure 1A:
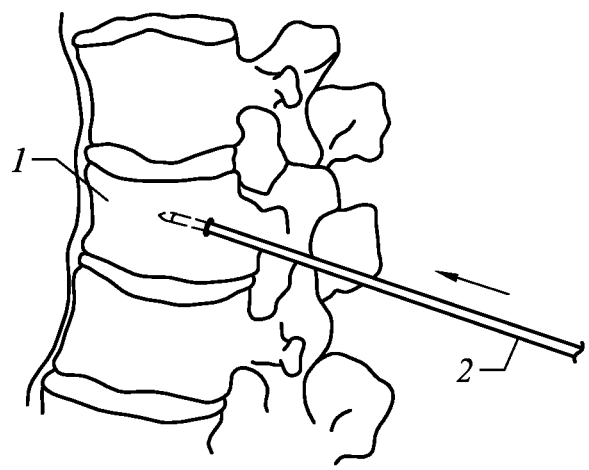
FIGS. 1A-1H illustrate steps of a spinal surgical procedure in accordance with the present invention.

A method for removing a bone tumor is described in FIGS. 1A to 1H. Referring first to FIG. 1A, a portion of the spine is shown. In particular, three vertebral bodies are shown. In an application, the diseased vertebral body 1 is identified and an introducer needle 2 having an obturator is inserted into the vertebral body.

The introducer needle 2 may be a metallic needle having a hollow shaft. It may have a diameter from 0.5 to 5 mm, or perhaps up to 10 mm. Its length may vary. Its length may range from 3 to 8 inches, and perhaps up to 15 inches, depending on the type of procedure. For example, the length will vary depending on the level to be treated and the size of the patient.

A sharp or pointed obturator is provided to prevent tissue from filling the introducer needle as well as facilitate penetration through the hard cortical bone. The obturator may comprise a radiopaque material or it may be made of a plastic. The obturator may be rigid and it may have various tip configurations to facilitate penetration of different types of tissue.

Figure 1B:
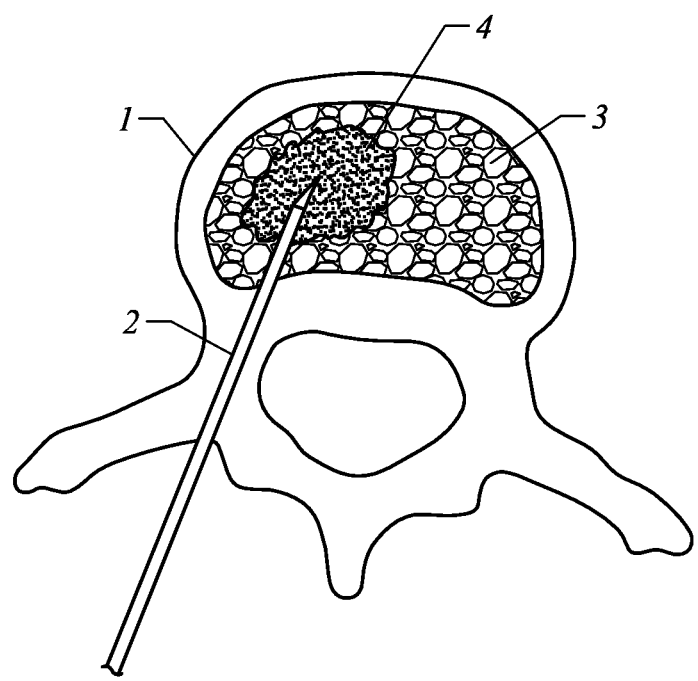

As shown in FIG. 1B, the introducer needle is extended through the pedicle, the cortical bone tissue, the cancellous bone tissue 3, and ultimately into or near the tumor 4 to be removed.

Figure 1C:
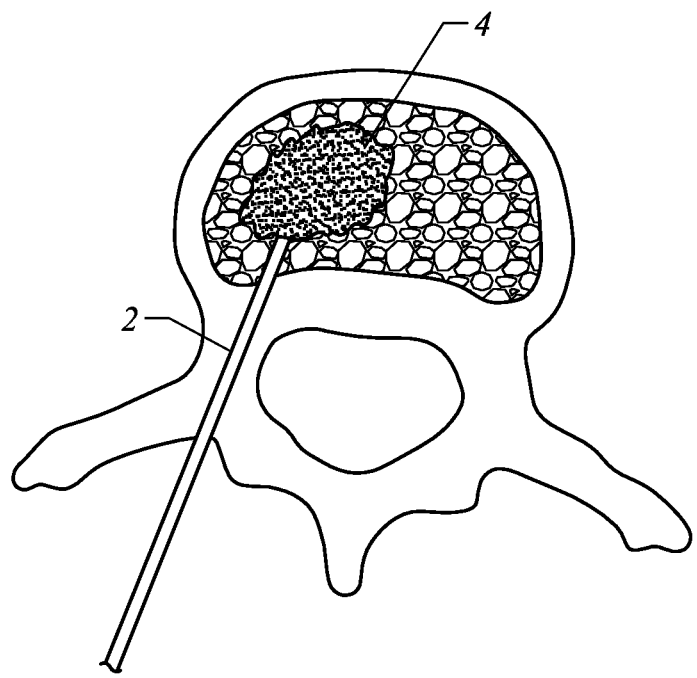

FIG. 1C shows the introducer needle touching the tumor with the obturator removed.

Figure 1D:
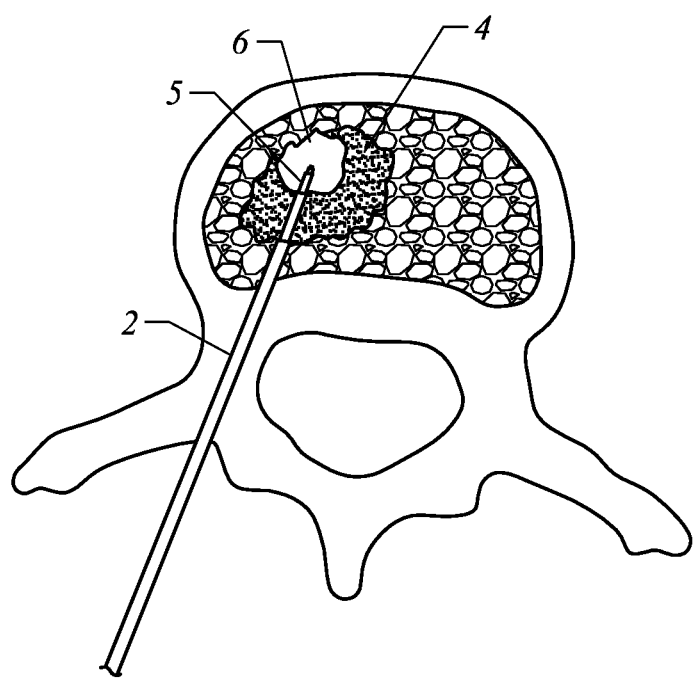
Figure 2A:
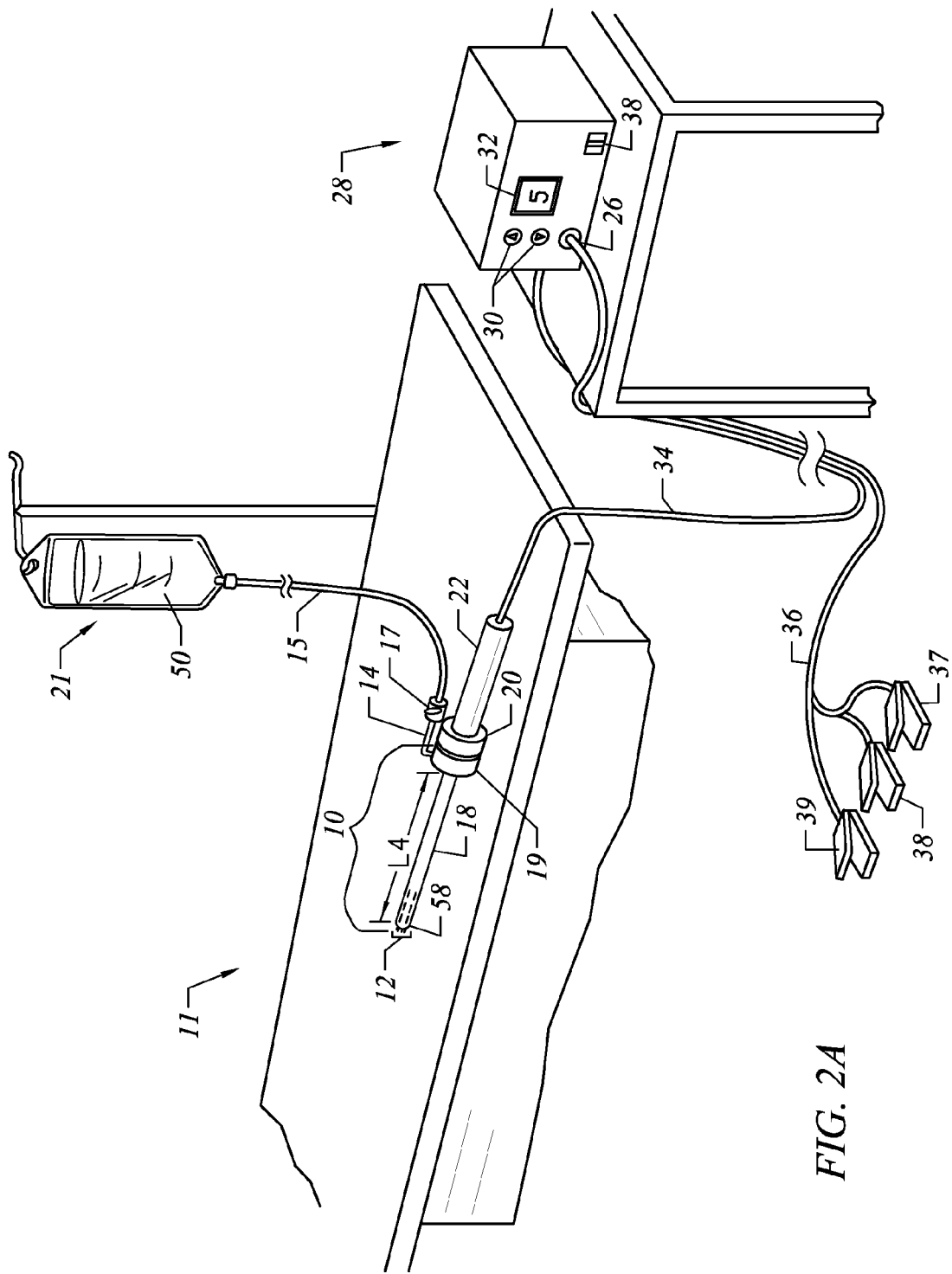
FIG. 2A is a perspective view of an electrosurgical system incorporating a power supply and an electrosurgical probe for tissue ablation, resection, incision, contraction and for vessel hemostasis.

FIG. 1D shows insertion of an electrosurgical probe 5, described more fully in connection with FIG. 2A et seq. Also, another probe suitable for use with this method is described in co pending patent application U.S. patent application Ser. No. 10/613,115, filed Jul. 3, 2003, incorporated by reference herein in its entirety.

The probe 5 is configured to apply energy to ablate tissue within a bone body, creating a void or space 6. In particular, the probe 5 contains at least one active electrode that is connected to a radiofrequency source. Application of a voltage difference between the active electrode and a return electrode disintegrates the tumor tissue into harmless components, leaving a space 6. Unlike other technologies using radio frequency energy, however, the present invention does not leave the tissue in place to be absorbed by the bone body over time in a slow eventual manner. Instead, the present invention ablates the tissue such that the tissue is immediately removed. As will be discussed in more detail below, and while not being bound to theory, the mechanism of action of the present invention is related to formation of a plasma at the probe tip.

Figure 1E:
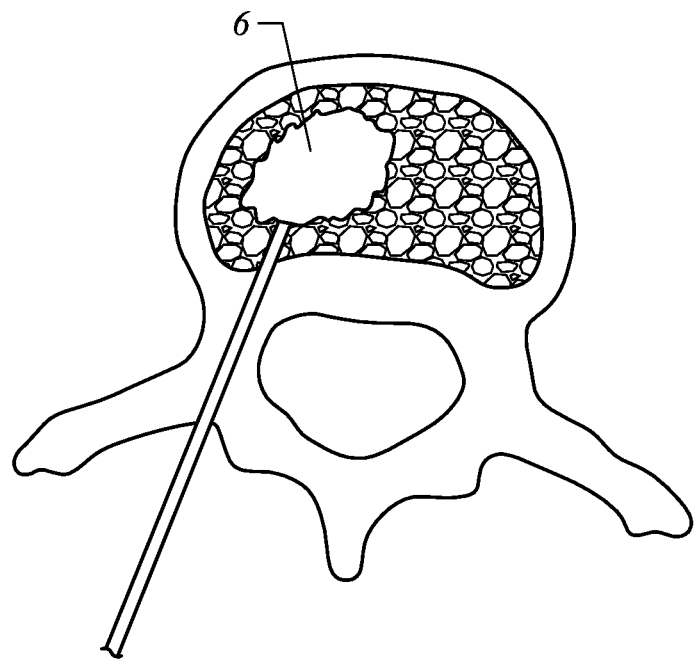

FIG. 1E shows the tumor removed leaving a large open space 6. Once the tumor is removed, it is desirable to stabilize the vertebral body. An open space, crack, fragment, etc. can facilitate spinal collapse resulting in serious pain, if not dehabilitation.

Figure 1F:
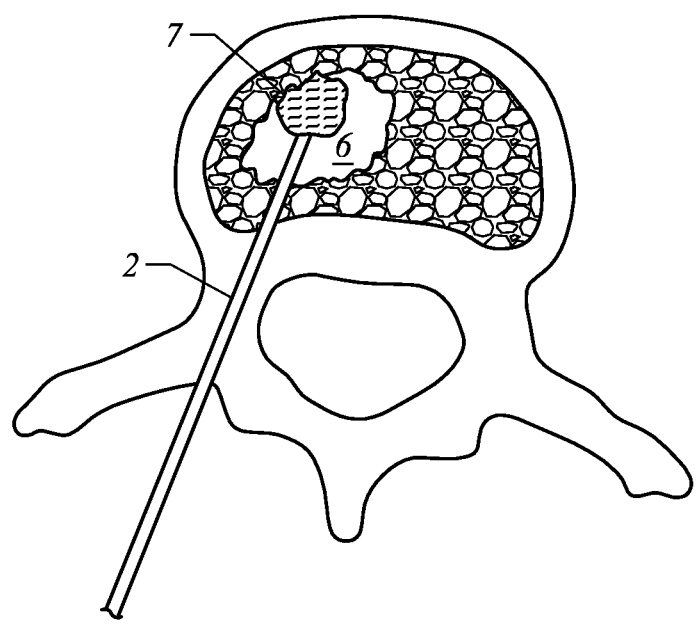

Accordingly, a vertebroplasty may desirably be performed as shown in FIG. 1F. In particular, a flowable bone cement 7 is injected into the space 6. A suitable cement injection system may include a connector that cooperates with the introducer needle 2. An example of a cement delivery system is EZFLOW™ CEMENT DELIVERY SYSTEM, manufactured by Parallax Medical Inc., Scotts Valley Calif.

Figure 1G:
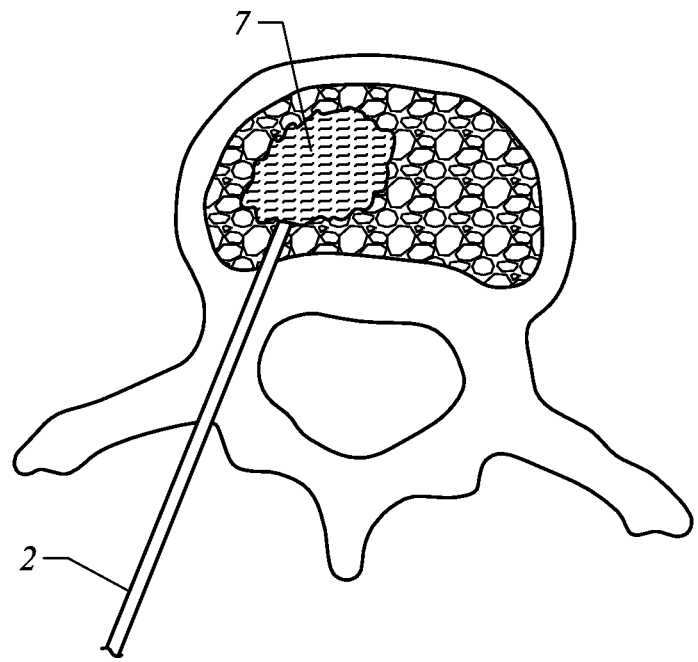
Figure 1H:
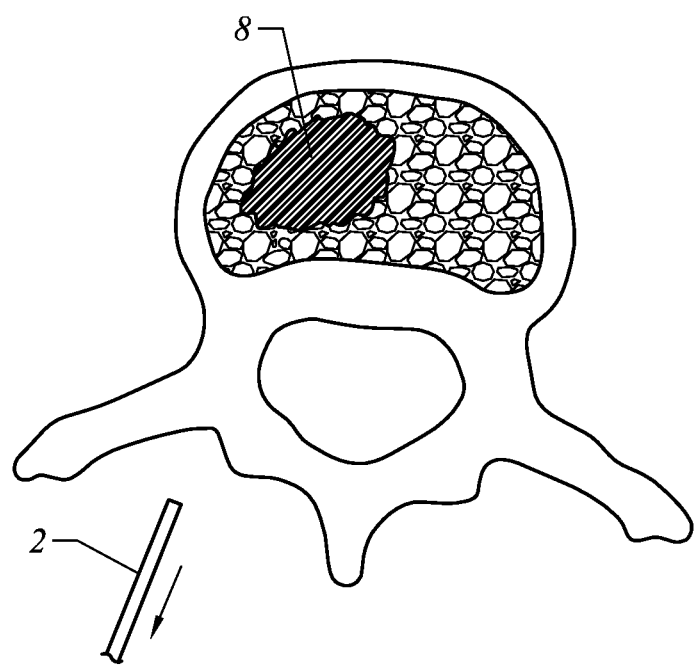

FIG. 1G indicates the space 6 filled with bone cement 7. Overtime, the bone cement will harden forming a solidified mass as shown in FIG. 1H. In some cases, the bone cement may permeate the rest of the vertebral body. Examples of bone cement are PMMA type acrylic resins such as SECOUR™, manufactured by Parallax Medical Inc., Scotts Valley, Calif. However, a wide variety of stabilizing material may be used to fill the space, 6 some of which having radio pacifiers to increase visualization of the flow. Specific aspects of the apparatus, system, and kits for performing various procedures to remove tissue within a bone body are described in more detail below.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site. Since the vapor layer or vaporized region has a relatively high electrical impedance, it minimizes the current flow into the electrically conductive fluid. This ionization, under the conditions described herein, induces the discharge of energetic electrons and photons from the vapor layer and to the surface of the target tissue. A more detailed description of this phenomena, termed Coblation® can be found in commonly assigned U.S. Pat. No. 5,697,882 the complete disclosure of which is incorporated herein by reference.

Applicant believes that the principle mechanism of tissue removal in the Coblation® mechanism of the present invention is energetic electrons or ions that have been energized in a plasma adjacent to the active electrode(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995), the complete disclosure of which is incorporated herein by reference. When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In one method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 eV to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 eV to 5 eV to break (typically on the order of about 8 eV). Accordingly, the present invention in its current configuration generally does not ablate or remove such fatty tissue. However, the present invention may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in U.S. Pat. No. 6,355,032, filed Feb. 27, 1998, the complete disclosure of which is incorporated herein by reference.

In yet other embodiments, the present invention provides systems, apparatus and methods for selectively removing tumors, e.g., spinal tumors, facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the active electrode(s) and one or more return electrode(s) to volumetrically remove at least a portion of the tissue cells in the tumor through the dissociation or disintegration of organic molecules into non-viable atoms and molecules. The present invention may provide an immediate removal of tissue. Specifically, the present invention converts the solid tissue cells into non-condensable gases that are no longer intact or viable, and thus, not capable of spreading viable tumor particles to other portions of the patient's bone, vessel or brain or to the surgical staff. The high frequency voltage is preferably selected to effect controlled removal of these tissue cells while minimizing substantial tissue necrosis to surrounding or underlying tissue. A more complete description of this phenomena can be found in U.S. patent application Ser. No. 09/109,219, filed Jun. 30, 1998, the complete disclosure of which is incorporated herein by reference.

The electrosurgical probe or catheter of the present invention can comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The active electrode(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in and around the spinal cord, however, makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the active electrode(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0 or by using a high velocity stream of abrasive particles (e.g., grit blasting) to create asperities on the surface of an elongated electrode. A more detailed description of such electrode configurations can be found in U.S. Pat. No. 5,843,019, the complete disclosure of which is incorporated herein by reference.

The return electrode is typically spaced proximally from the active electrode(s) a suitable distance to avoid electrical shorting between the active and return electrodes in the presence of electrically conductive fluid. In most of the embodiments described herein, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

The current flow path between the active electrodes and the return electrode(s) may be generated by submerging the tissue site in an electrical conducting fluid (e.g., within a viscous fluid, such as an electrically conductive gel) or by directing an electrically conductive fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, previously incorporated herein by reference. Alternatively, the body's natural conductive fluids, such as blood or extracellular saline, may be sufficient to establish a conductive path between the return electrode(s) and the active electrode(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply, or generator, may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, U.S. Pat. No. 6,235,020, filed Apr. 10, 1998, the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, U.S. Pat. No. 6,190,381, filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath, or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

Apparatuses may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The tip region of the instrument may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals affects shrinking, cutting, removing, ablating, shaping, contracting or otherwise modifying the target tissue. In some embodiments of the present invention, the tissue volume over which energy is dissipated (i.e., a high current density exists) may be more precisely controlled, for example, by the use of a multiplicity of small active electrodes whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per active electrode) below 50 mm$^2$ for electrode arrays and as large as 75 mm$^2$ for single electrode embodiments. In multiple electrode array embodiments, the contact area of each active electrode is typically in the range from 0.0001 mm$^2$ to 1 mm$^2$, and more preferably from 0.001 mm$^2$ to 0.5 mm$^2$. The circumscribed area of the electrode array or active electrode is in the range from 0.25 mm$^2$ to 75 mm$^2$, preferably from 0.5 mm$^2$ to 40 mm$^2$. In multiple electrode embodiments, the array will usually include at least two isolated active electrodes, often at least five active electrodes, often greater than 10 active electrodes and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or active electrode(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

It should be clearly understood that the invention is not limited to electrically isolated active electrodes, or even to a plurality of active electrodes. For example, the array of active electrodes may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

The electrically conductive fluid should have a threshold conductivity to provide a suitable conductive path between the return electrode and the active electrode(s). The electrical conductivity of the fluid (in units of millisiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation). Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular spinal surgery, neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, both of which were filed Apr. 10, 1998, the complete disclosures of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from the active electrode into the low resistance medium (e.g., saline irrigant or blood).

Referring to FIG. 2A, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 211 (see FIG. 4) in the probe 10 for aspirating the target site.

As shown, probe 10 generally includes a proximal handle 19 and an elongate shaft 18 having an array 12 of active electrodes 58 at its distal end. A connecting cable 34 has a connector 26 for electrically coupling the active electrodes 58 to power supply 28. The active electrodes 58 are electrically isolated from each other and each of electrodes 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site. Fluid supply tube 15 may be connected to a suitable pump (not shown), if desired.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to active electrodes 58. In an exemplary embodiment, first foot pedal 37 is used to place the power supply into the "ablation" mode and second foot pedal 38 places power supply 28 into the "sub-ablation" mode (e.g., for coagulation or contraction of tissue). The third foot pedal 39 allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the active electrodes to avoid vaporization of the electrically conductive fluid and subsequent molecular dissociation of the tissue. The surgeon may automatically toggle the power supply between the ablation and sub-ablation modes by alternately stepping on foot pedals 37, 38, respectively. In some embodiments, this allows the surgeon to quickly move between coagulation/thermal heating and ablation in situ, without having to remove his/her concentration from the surgical field or without having to request an assistant to switch the power supply. By way of example, as the surgeon is sculpting tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2B:
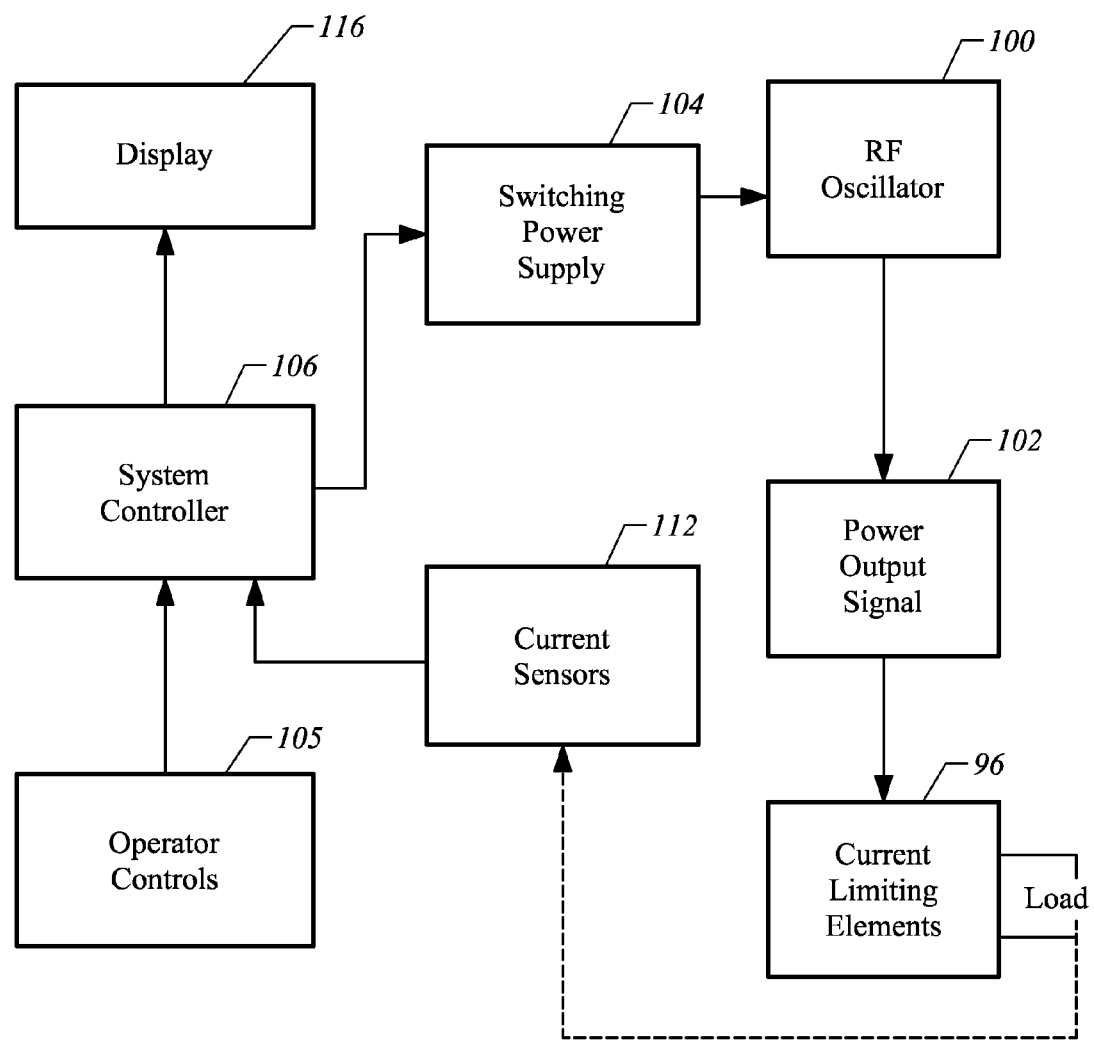
FIG. 2B schematically illustrates one embodiment of a power supply according to the present invention.
Figure 3:
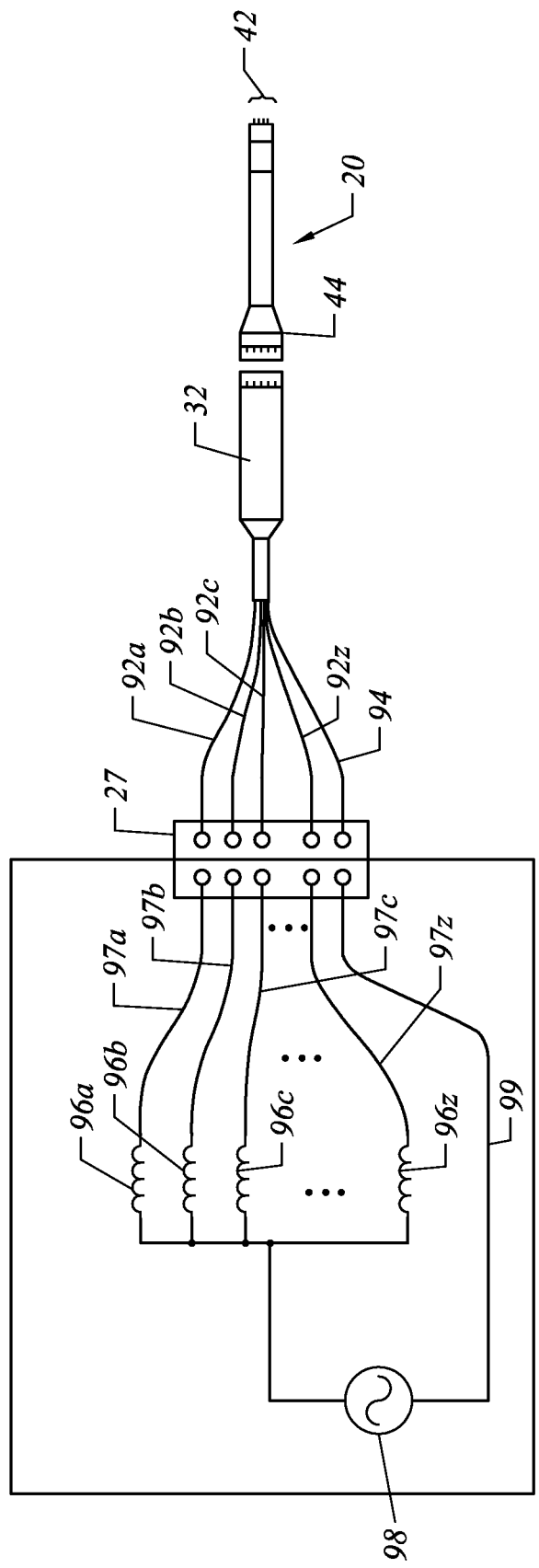
FIG. 3 illustrates an electrosurgical system incorporating a plurality of active electrodes and associated current limiting elements.

Referring now to FIGS. 2B and 3, a representative high frequency power supply for use according to the principles of the present invention will now be described. The high frequency power supply of the present invention is configured to apply a high frequency voltage of about 10 volts RMS to 500 volts RMS between one or more active electrodes (and/or coagulation electrode) and one or more return electrodes. In the exemplary embodiment, the power supply applies about 70 volts RMS to 350 volts RMS in the ablation mode and about 20 volts to 90 volts in a subablation mode, preferably 45 volts to 70 volts in the subablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being treated, and/or the maximum allowed temperature selected for the probe tip. The power supply allows the user to select the voltage level according to the specific requirements of a particular procedure, e.g., spinal surgery, arthroscopic surgery, dermatological procedure, ophthalmic procedures, open surgery, or other endoscopic surgery procedure.

As shown in FIG. 2B, the power supply generally comprises a radio frequency (RF) power oscillator 70 having output connections for coupling via a power output signal 71 to the load impedance, which is represented by the electrode assembly when the electrosurgical probe is in use. In the representative embodiment, the RF oscillator operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 71 is designed to incur minimal voltage decrease (i.e., sag) under load. This improves the applied voltage to the active electrodes and the return electrode, which improves the rate of volumetric removal (ablation) of tissue.

Power is supplied to RF oscillator 70 by a switching power supply 72 coupled between the power line and the RF oscillator rather than a conventional transformer. The switching power supply 72 allows power supply 28 to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 72 operates at about 100 kHz.

A controller 74 coupled to the operator controls 73 (i.e., foot pedals and voltage selector) and display 76, is connected to a control input of the switching power supply 72 for adjusting the generator output power by supply voltage variation. The controller 74 may be a microprocessor or an integrated circuit. The power supply may also include one or more current sensors 75 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield," thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the active electrodes 102 (see FIG. 4).

Alternatively, in one embodiment, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending International Application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel). Power output signal may also be coupled to a plurality of current limiting elements 96, which are preferably located on the daughter board since the current limiting elements may vary depending on the application. A more complete description of a representative power supply can be found in commonly assigned U.S. Pat. No. 6,142,992, previously incorporated herein by reference.

Figure 4:
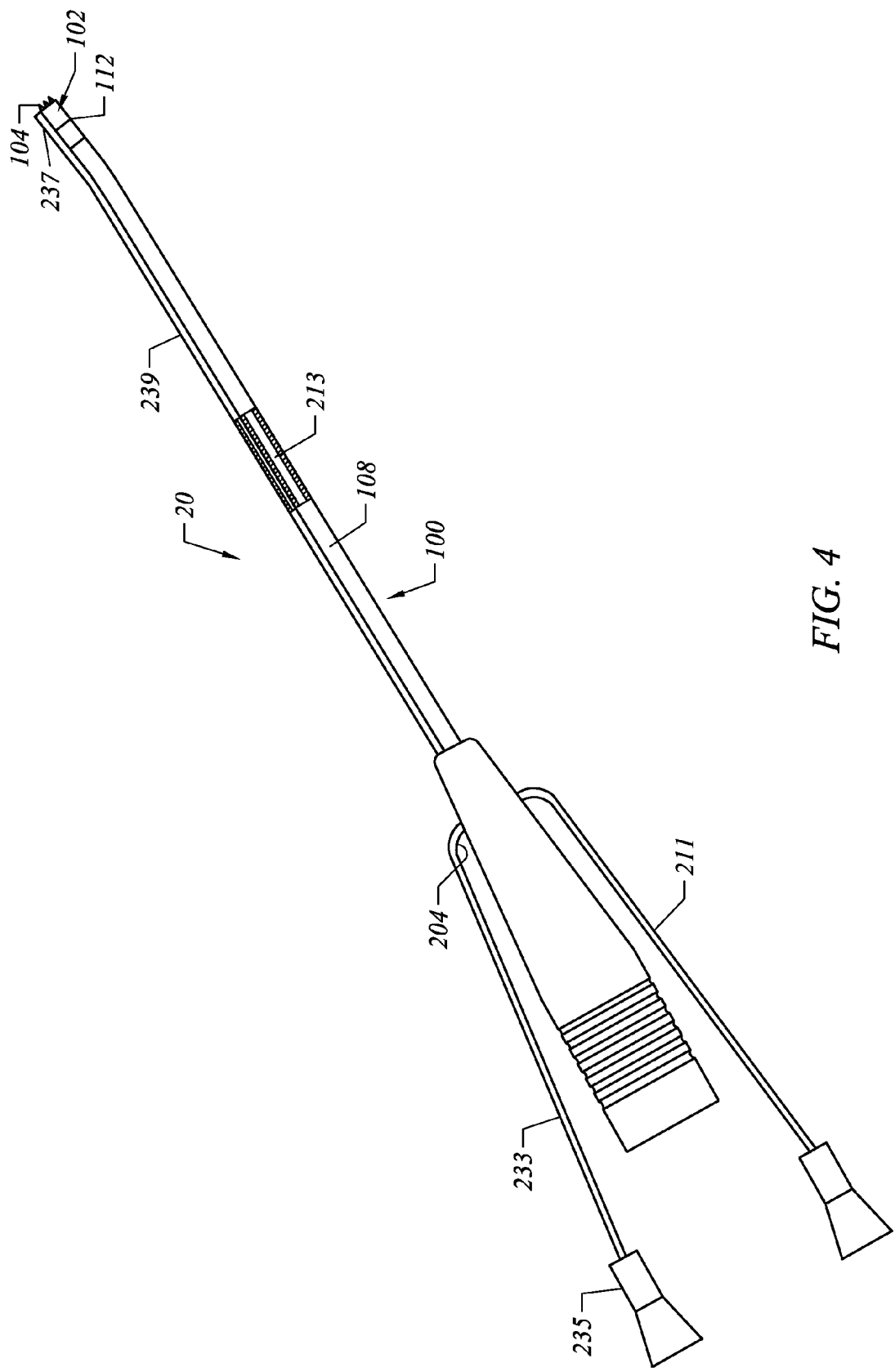
FIG. 4 is a side view of an electrosurgical probe.
Figure 5:
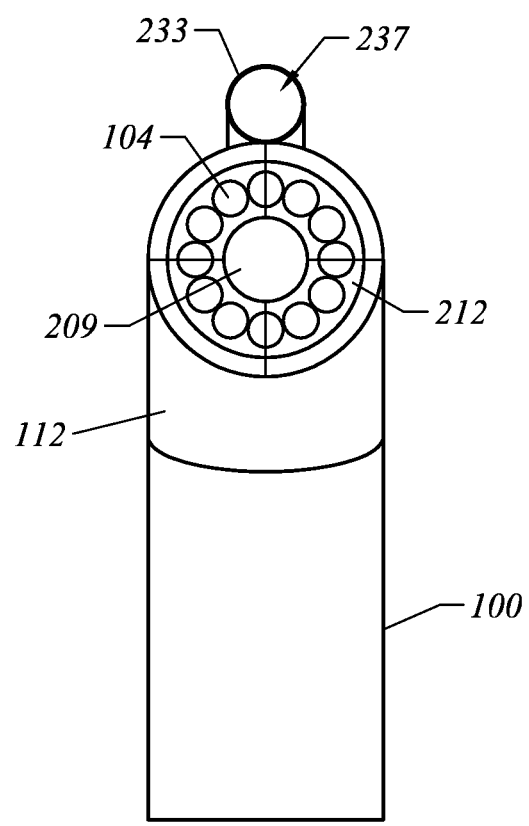
FIG. 5 is a view of the distal end portion of the probe of FIG. 4.
Figure 6:
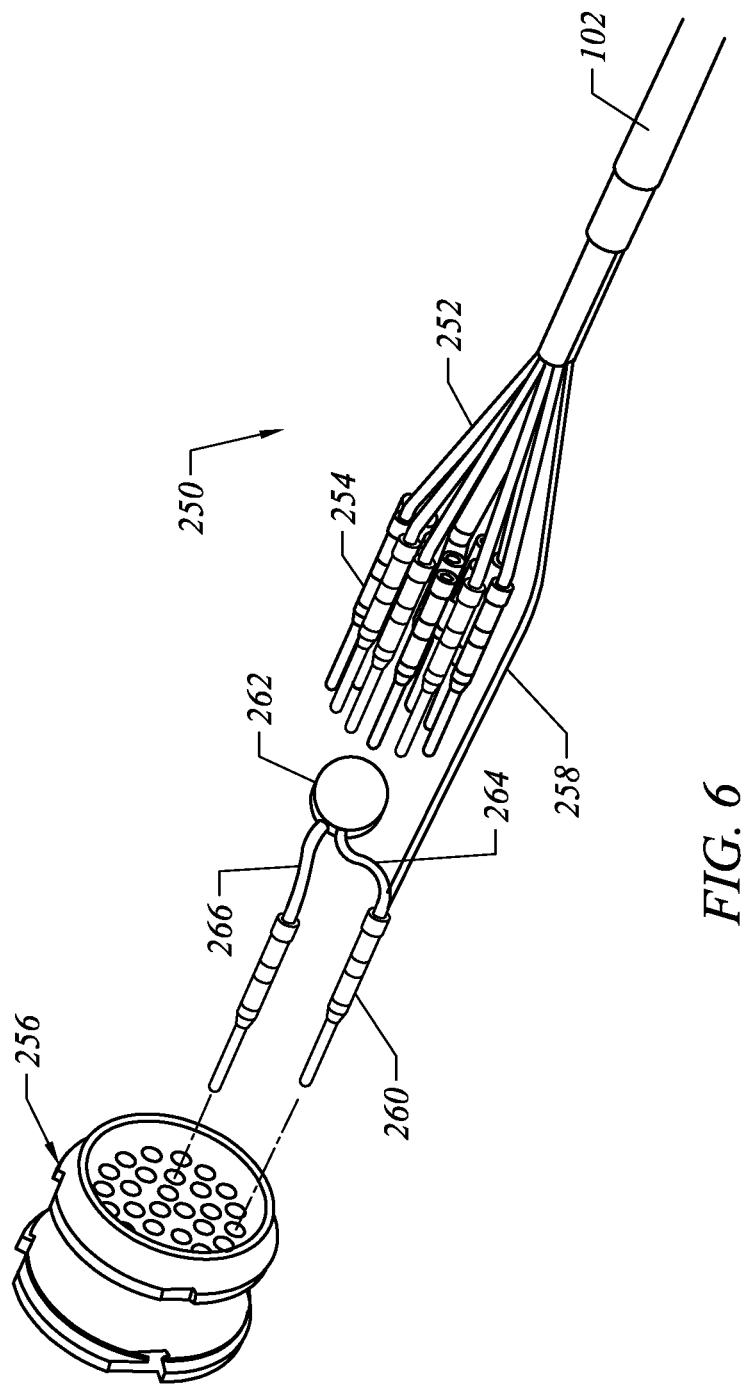
FIG. 6 is an exploded view of a proximal portion of an electrosurgical probe.

FIGS. 4-6 illustrate an exemplary electrosurgical probe 20 constructed according to the principles of the present invention. As shown in FIG. 4, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis. Alternatively, the return electrode may comprise an annular band coupled to an insulating shaft and having a connector extending within the shaft to its proximal end.

Handle 204 typically comprises a plastic material that is easily molded into a suitable shape for handling by the surgeon. Handle 204 defines an inner cavity (not shown) that houses the electrical connections 250 (FIG. 6), and provides a suitable interface for connection to an electrical connecting cable distal portion 22 (see FIG. 2A) Electrode support member 102 extends from the distal end of shaft 100 (usually about 1 mm to 20 mm), and provides support for a plurality of electrically isolated active electrodes 104 (see FIG. 5). As shown in FIG. 4, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, tubing 239 is a tube that extends along the exterior of shaft 100 to a point just distal of return electrode 112 (see FIG. 5). In this embodiment, the fluid is directed through an opening 237 past return electrode 112 to the active electrodes 104. Probe 20 may also include a valve 17 (FIG. 2A) or equivalent structure for controlling the flow rate of the electrically conductive fluid to the target site.

As shown in FIG. 4, the distal portion of shaft 100 is preferably bent to improve access to the operative site of the tissue being treated. Electrode support member 102 has a substantially planar tissue treatment surface 212 (FIG. 5) that is usually at an angle of about 10 degrees to 90 degrees relative to the longitudinal axis of shaft 100, preferably about 30 degrees to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in U.S. Pat. No. 5,697,909, the complete disclosure of which has previously been incorporated herein by reference. Alternatively, the shaft 100 of the present invention may be bent by the physician to the appropriate angle using a conventional bending tool or the like.

In the embodiment shown in FIGS. 4 to 6, probe 20 includes a return electrode 112 for completing the current path between active electrodes 104 and a high frequency power supply 28 (see FIG. 2A). As shown, return electrode 112 preferably comprises an exposed portion of shaft 100 shaped as an annular conductive band near the distal end of shaft 100 slightly proximal to tissue treatment surface 212 of electrode support member 102, typically about 0.5 mm to 10 mm and more preferably about 1 mm to 10 mm. Return electrode 112 or shaft 100 is coupled to a connector 258 that extends to the proximal end of probe 10/20, where it is suitably connected to power supply 28 (FIG. 2A).

As shown in FIG. 4, return electrode 112 is not directly connected to active electrodes 104. To complete this current path so that active electrodes 104 are electrically connected to return electrode 112, an electrically conductive fluid (e.g., isotonic saline) is caused to flow therebetween. In the representative embodiment, the electrically conductive fluid is delivered through fluid tube 233 to opening 237, as described above. Alternatively, the conductive fluid may be delivered by a fluid delivery element (not shown) that is separate from probe 20. In arthroscopic surgery, for example, the target area of the joint will be flooded with isotonic saline and the probe 90 will be introduced into this flooded target area. Electrically conductive fluid can be continually resupplied to maintain the conduction path between return electrode 112 and active electrodes 104. In other embodiments, the distal portion of probe 20 may be dipped into a source of electrically conductive fluid, such as a gel or isotonic saline, prior to positioning at the target site. Applicant has found that the surface tension of the fluid and/or the viscous nature of a gel allows the conductive fluid to remain around the active and return electrodes for long enough to complete its function according to the present invention, as described below. Alternatively, the conductive fluid, such as a gel, may be applied directly to the target site.

In alternative embodiments, the fluid path may be formed in probe 90 by, for example, an inner lumen or an annular gap between the return electrode and a tubular support member within shaft 100 (see FIGS. 8A and 8B). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in U.S. Pat. No. 5,697,281, the complete disclosure of which has previously been incorporated herein by reference.

Referring to FIG. 5, the electrically isolated active electrodes 104 are spaced apart over tissue treatment surface 212 of electrode support member 102. The tissue treatment surface and individual active electrodes 104 will usually have dimensions within the ranges set forth above. In the representative embodiment, the tissue treatment surface 212 has a circular cross-sectional shape with a diameter in the range of 1 mm to 20 mm. The individual active electrodes 104 preferably extend outward from tissue treatment surface 212 by a distance of about 0.1 mm to 4 mm, usually about 0.2 mm to 2 mm. Applicant has found that this configuration increases the high electric field intensities and associated current densities around active electrodes 104 to facilitate the ablation and shrinkage of tissue as described in detail above.

In the embodiment of FIGS. 4 to 6, the probe includes a single, larger opening 209 in the center of tissue treatment surface 212, and a plurality of active electrodes (e.g., about 3-15) around the perimeter of surface 212 (see FIG. 5). Alternatively, the probe may include a single, annular, or partially annular, active electrode at the perimeter of the tissue treatment surface. The central opening 209 is coupled to a suction lumen (not shown) within shaft 100 and a suction tube 211 (FIG. 4) for aspirating tissue, fluids and/or gases from the target site. In this embodiment, the electrically conductive fluid generally flows radially inward past active electrodes 104 and then back through the opening 209. Aspirating the electrically conductive fluid during surgery allows the surgeon to see the target site, and it prevents the fluid from flowing into the patient's body.

Of course, it will be recognized that the distal tip of an electrosurgical probe of the invention, e.g. probe 10/20/90, may have a variety of different configurations. For example, the probe may include a plurality of openings 209 around the outer perimeter of tissue treatment surface 212 (see FIG. 7B). In this embodiment, the active electrodes 104 extend distally from the center of tissue treatment surface 212 such that they are located radially inward from openings 209. The openings are suitably coupled to fluid tube 233 for delivering electrically conductive fluid to the target site, and suction tube 211 for aspirating the fluid after it has completed the conductive path between the return electrode 112 and the active electrodes 104.

FIG. 6 illustrates the electrical connections 250 within handle 204 for coupling active electrodes 104 and return electrode 112 to the power supply 28. As shown, a plurality of wires 252 extend through shaft 100 to couple active electrodes 104 to a plurality of pins 254, which are plugged into a connector block 256 for coupling to a connecting cable distal end 22 (FIG. 2A). Similarly, return electrode 112 is coupled to connector block 256 via a wire 258 and a plug 260.

According to the present invention, the probe 20 further includes an identification element that is characteristic of the particular electrode assembly so that the same power supply 28 can be used for different electrosurgical operations. In one embodiment, for example, the probe (e.g., 20) includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conducting medium and/or ablation of the soft tissue at the target site. In some embodiments, the voltage reduction element allows the power supply 28 to apply two different voltages simultaneously to two different electrodes (see FIG. 7D). In other embodiments, the voltage reduction element primarily allows the electrosurgical probe to be compatible with various electrosurgical generators supplied by ArthroCare Corporation (Sunnyvale, Calif.) that are adapted to apply higher voltages for ablation or vaporization of tissue. For thermal heating or coagulation of tissue, for example, the voltage reduction element will serve to reduce a voltage of about 100 volts rms to 170 volts rms (which is a setting of 1 or 2 on the ArthroCare Model 970 and 980 (i.e., 2000) Generators) to about 45 volts rms to 60 volts rms, which is a suitable voltage for coagulation of tissue without ablation (e.g., molecular dissociation) of the tissue.

Of course, for some procedures, the probe will typically not require a voltage reduction element. Alternatively, the probe may include a voltage increasing element or circuit, if desired. Alternatively or additionally, the cable 34 and/or cable distal end 22 that couples the power supply 28 to the probe may be used as a voltage reduction element. The cable has an inherent capacitance that can be used to reduce the power supply voltage if the cable is placed into the electrical circuit between the power supply, the active electrodes and the return electrode. In this embodiment, the cable distal end 22 may be used alone, or in combination with one of the voltage reduction elements discussed above, e.g., a capacitor. Further, it should be noted that the present invention can be used with a power supply that is adapted to apply a voltage within the selected range for treatment of tissue. In this embodiment, a voltage reduction element or circuitry may not be desired.

Figure 7A:
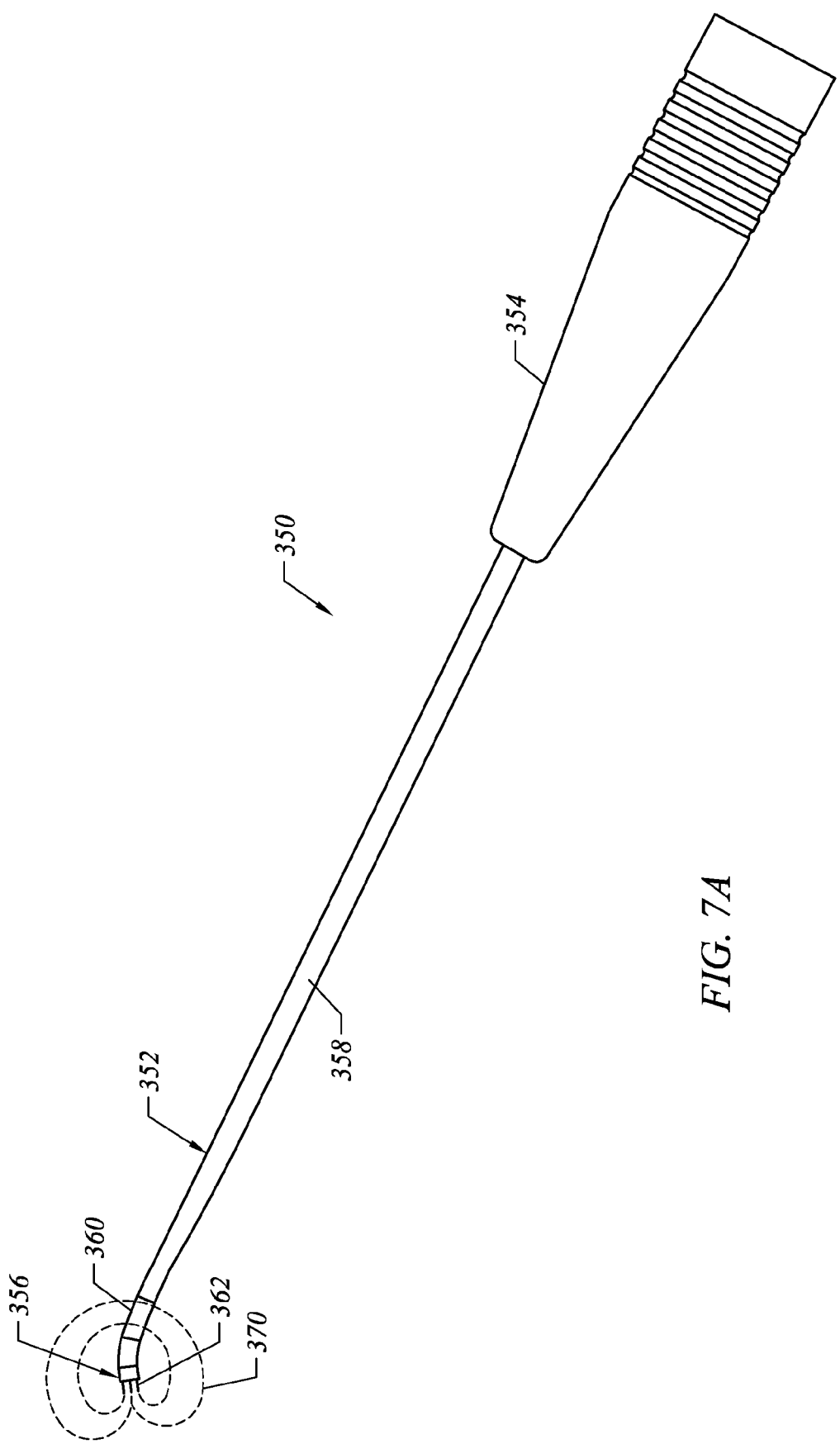
FIGS. 7A-7D illustrate four embodiments of electrosurgical probes designed for treating spinal defects.

FIGS. 7A to 7D illustrate embodiments of an electrosurgical probe 350 specifically designed for the treatment of herniated or diseased spinal discs. Referring to FIG. 7A, probe 350 comprises an electrically conductive shaft 352, a handle 354 coupled to the proximal end of shaft 352 and an electrically insulating support member 356 at the distal end of shaft 352. Probe 350 further includes a shrink wrapped insulating sleeve 358 over shaft 352, and an exposed portion of shaft 352 that functions as the return electrode 360. In the representative embodiment, probe 350 comprises a plurality of active electrodes 362 extending from the distal end of support member 356. As shown, return electrode 360 is spaced a further distance from active electrodes 362 than in the embodiments described above. In this embodiment, the return electrode 360 is spaced a distance of about 2.0 mm to 50 mm, preferably about 5 mm to 25 mm from active electrodes 362. In addition, return electrode 360 has a larger exposed surface area than in previous embodiments, having a length in the range of about 2.0 mm to 40 mm, preferably about 5 mm to 20 mm. Accordingly, electric current passing from active electrodes 362 to return electrode 360 will follow a current flow path 370 that is further away from shaft 352 than in the previous embodiments. In some applications, this current flow path 370 results in a deeper current penetration into the surrounding tissue with the same voltage level, and thus increased thermal heating of the tissue. As discussed above, this increased thermal heating may have advantages in some applications of treating disc or other spinal abnormalities. Typically, it is desired to achieve a tissue temperature in the range of about 60° C. to 100° C. to a depth of about 0.2 mm to 5 mm, usually about 1 mm to 2 mm. The voltage required for this thermal damage will partly depend on the electrode configurations, the conductivity of the tissue and the area immediately surrounding the electrodes, the time period in which the voltage is applied and the depth of tissue damage desired. With the electrode configurations described in FIGS. 7A-7D, the voltage level for thermal heating will usually be in the range of about 20 volts rms to 300 volts rms, preferably about 60 volts rms to 200 volts rms. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which is undesirable.

In alternative embodiments, the electrosurgical system used in conjunction with probe 350 may include a dispersive return electrode 450 (see FIG. 8) for switching between bipolar and monopolar modes. In this embodiment, the system will switch between an ablation mode, where the dispersive pad 450 is deactivated and voltage is applied between active and return electrodes 362, 360, and a subablation or thermal heating mode, where the active electrode(s) 362 are deactivated and voltage is applied between the dispersive pad 450 and the return electrode 360. In the subablation mode, a lower voltage is typically applied and the return electrode 360 functions as the active electrode to provide thermal heating and/or coagulation of tissue surrounding return electrode 360.

Figure 7B:
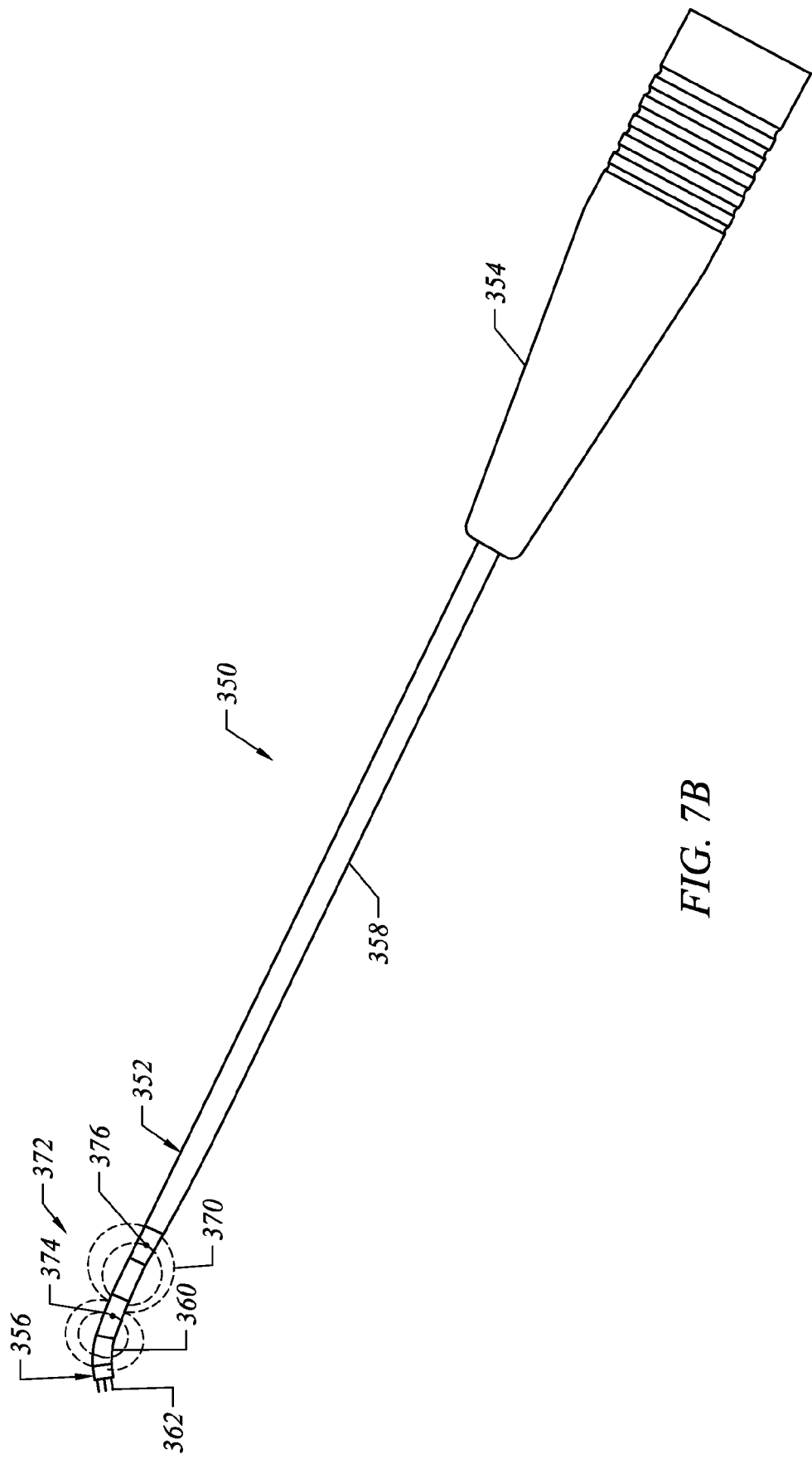

FIG. 7B illustrates yet another probe. As shown, electrosurgical probe 350 comprises an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes two additional electrodes 374, 376 spaced axially on either side of return electrode 360. Electrodes 374, 376 are typically spaced about 0.5 mm to 25 mm, preferably about 1 mm to 5 mm from return electrode 360. In the representative embodiment, the additional electrodes 374, 376 are exposed portions of shaft 352, and the return electrode 360 is electrically insulated from shaft 352 such that a voltage difference may be applied between electrodes 374, 376 and electrode 360. In this embodiment, probe 350 may be used in at least two different modes, an ablation mode and a subablation or thermal heating mode. In the ablation mode, voltage is applied between active electrode(s) 362 and return electrode 360 in the presence of electrically conductive fluid, as described above. In the ablation mode, electrodes 374, 376 are deactivated. In the thermal heating or coagulation mode, active electrode(s) 362 are deactivated and a voltage difference is applied between electrodes 374, 376 and electrode 360 such that a high frequency current 370 flows therebetween, as shown in FIG. 7B. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 372, 374.

Figure 7C:
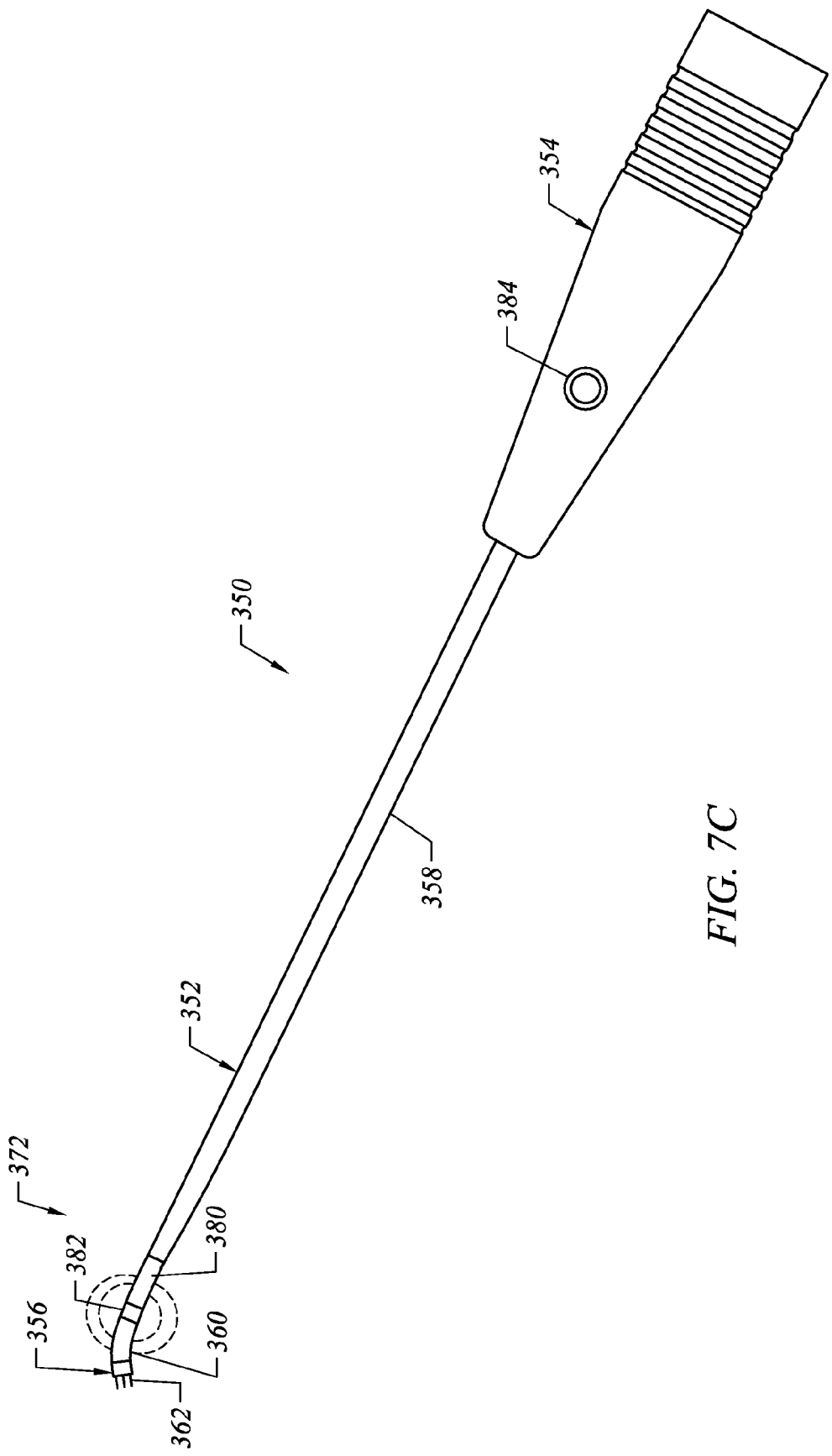

FIG. 7C illustrates another probe 350 incorporating an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes a second active electrode 380 separated from return electrode 360 by an electrically insulating spacer 382. In this embodiment, handle 354 includes a switch 384 for toggling probe 350 between at least two different modes, an ablation mode and a subablation or thermal heating mode. In the ablation mode, voltage is applied between active electrode(s) 362 and return electrode 360 in the presence of electrically conductive fluid, as described above. In the ablation mode, electrode 380 is deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 380.

Of course, it will be recognized that a variety of other embodiments may be used to accomplish similar functions as the embodiments described above. For example, electrosurgical probe 350 may include a plurality of helical bands formed around shaft 352, with one or more of the helical bands having an electrode coupled to the portion of the band such that one or more electrodes are formed on shaft 352 spaced axially from each other.

Figure 7D:
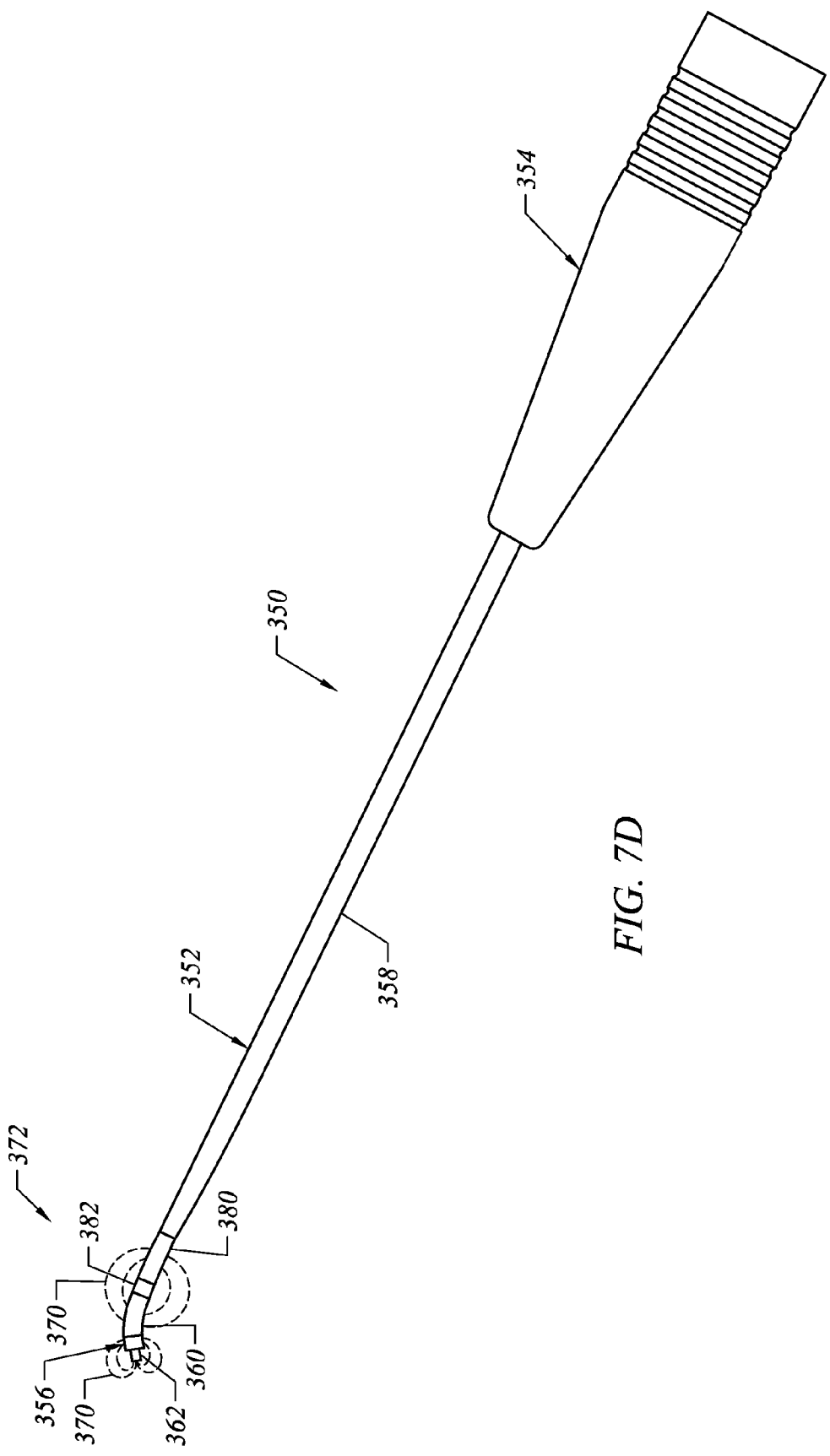

FIG. 7D illustrates another probe designed for channeling through tissue and creating lesions. This probe may be useful in a wide variety of applications such as, for example, treatment of spinal discs and/or snoring and sleep apnea. As shown, probe 350 is similar to the probe in FIG. 7C having a return electrode 360 and a third, coagulation electrode 380 spaced proximally from the return electrode 360. In this embodiment, active electrode 362 comprises a single electrode wire extending distally from insulating support member 356. Of course, the active electrode 362 may have a variety of configurations to increase the current densities on its surfaces, e.g., a conical shape tapering to a distal point, a hollow cylinder, loop electrode and the like. In the representative embodiment, support members 356 and 382 are constructed of a material, such as ceramic, glass, silicone and the like. The proximal support member 382 may also comprise a more conventional organic material as this support member 382 will generally not be in the presence of a plasma that would otherwise etch or wear away an organic material.

The probe 350 in FIG. 7D does not include a switching element. In this embodiment, all three electrodes are activated when the power supply is activated. The return electrode 360 has an opposite polarity from the active and coagulation electrodes 362, 380 such that current 370 flows from the latter electrodes to the return electrode 360 as shown. In the preferred embodiment, the electrosurgical system includes a voltage reduction element or a voltage reduction circuit for reducing the voltage applied between the coagulation electrode 380 and return electrode 360. The voltage reduction element allows the power supply 28 to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 362). At the same time, the voltage applied to the coagulation electrode 380 will be insufficient to ablate tissue. For thermal heating or coagulation of tissue, for example, the voltage reduction element will serve to reduce a voltage of about 100 volts rms to 300 volts rms to about 45 volts rms to 90 volts rms, which is a suitable voltage for coagulation of tissue without ablation (e.g., molecular dissociation) of the tissue.

In the representative embodiment, the voltage reduction element comprises a pair of capacitors forming a bridge divider (not shown) coupled to the power supply and coagulation electrode 380. The capacitors usually have a capacitance of about 200 pF to 500 pF (at 500 volts) and preferably about 300 pF to 350 pF (at 500 volts). Of course, the capacitors may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 350 may include a coded resistor (not shown) that is constructed to lower the voltage applied between the return and coagulation electrodes 360, 380, respectively. In addition, electrical circuits may be employed for this purpose.

Of course, for some procedures, the probe will typically not require a voltage reduction element. Alternatively, the probe may include a voltage increasing element or circuit, if desired. Alternatively or additionally, cable 22/34 that couples power supply 28 to the probe 90 may be used as a voltage reduction element. The cable has an inherent capacitance that can be used to reduce the power supply voltage if the cable is placed into the electrical circuit between the power supply, the active electrodes and the return electrode. In this embodiment, cable 22/34 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In one specific embodiment, the probe 350 is manufactured by first inserting an electrode wire (active electrode 362) through a ceramic tube (insulating member 356) such that a distal portion of the wire extends through the distal portion of the tube, and bonding the wire to the tube, typically with an appropriate epoxy. A stainless steel tube (return electrode 360) is then placed over the proximal portion of the ceramic tube, and a wire (e.g., nickel wire) is bonded, typically by spot welding, to the inside surface of the stainless steel tube. The stainless steel tube is coupled to the ceramic tube by epoxy, and the device is cured in an oven or other suitable heat source. A second ceramic tube (insulating member 382) is then placed inside of the proximal portion of the stainless steel tube, and bonded in a similar manner. The shaft 358 is then bonded to the proximal portion of the second ceramic tube, and an insulating sleeve (e.g. polyimide) is wrapped around shaft 358 such that only a distal portion of the shaft is exposed (i.e., coagulation electrode 380). The nickel wire connection will extend through the center of shaft 358 to connect return electrode 360 to the power supply. The active electrode 362 may form a distal portion of shaft 358, or it may also have a connector extending through shaft 358 to the power supply.

In use, the physician positions active electrode 362 adjacent to the tissue surface to be treated (e.g., a spinal disc). The power supply is activated to provide an ablation voltage between active and return electrodes 362, 360, respectively, and a coagulation or thermal heating voltage between coagulation and return electrodes 380, 360, respectively. An electrically conductive fluid can then be provided around active electrode 362, and in the junction between the active and return electrodes 360, 362 to provide a current flow path therebetween. This may be accomplished in a variety of manners, as discussed above. The active electrode 362 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 362. Once the physician has formed the channel to the appropriate depth, he or she will cease advancement of the active electrode, and will either hold the instrument in place for approximately 5 seconds to 30 seconds, or can immediately remove the distal tip of the instrument from the channel (see detailed discussion of this below). In either event, when the active electrode is no longer advancing, it will eventually stop ablating tissue.

Prior to entering the channel formed by the active electrode 362, an open circuit exists between return and coagulation electrodes 360, 380. Once coagulation electrode 380 enters this channel, electric current will flow from coagulation electrode 380, through the tissue surrounding the channel, to return electrode 360. This electric current will heat the tissue immediately surrounding the channel to coagulate any severed vessels at the surface of the channel. If the physician desires, the instrument may be held within the channel for a period of time to create a lesion around the channel, as discussed in more detail below.

Figure 8:
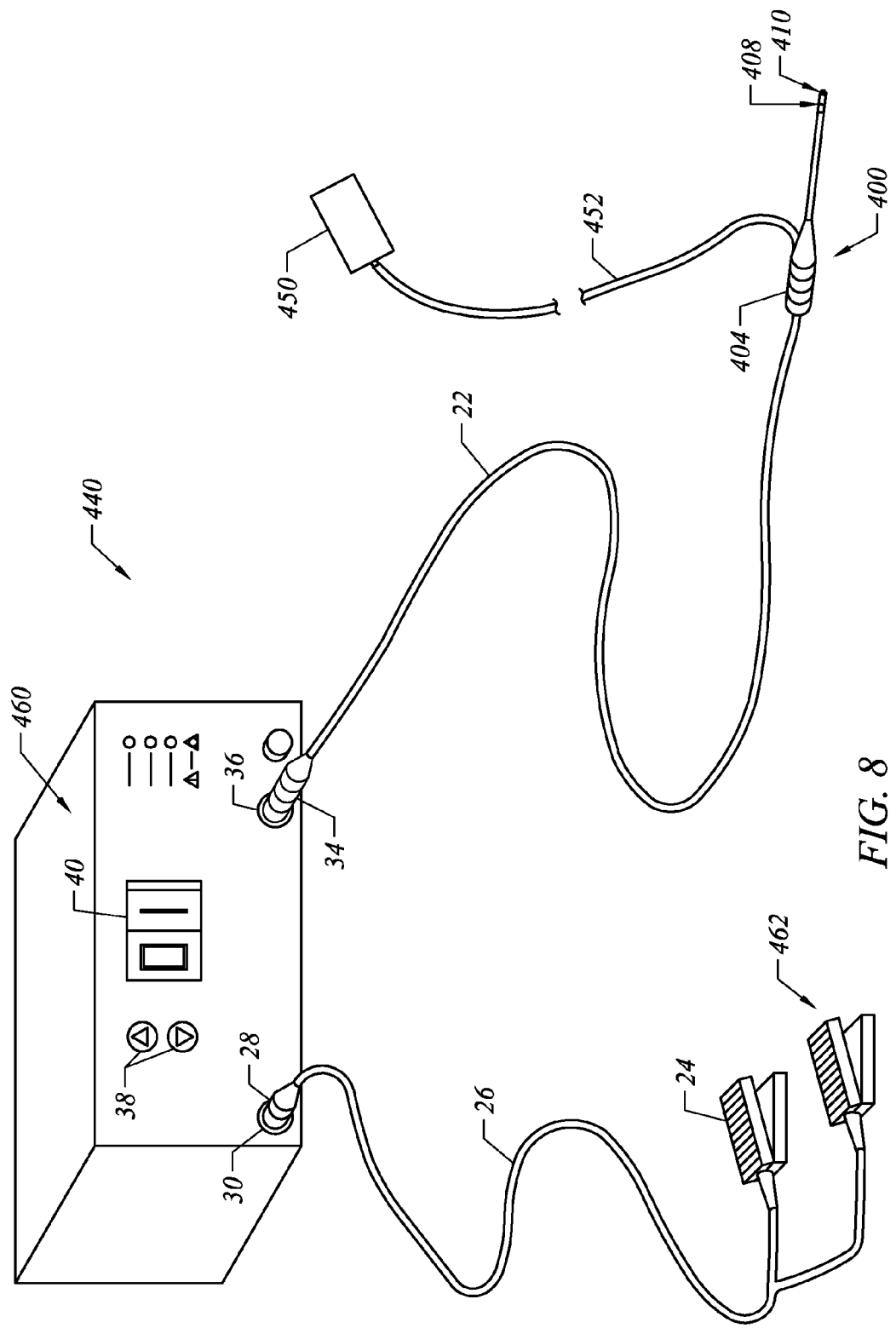
FIG. 8 illustrates an electrosurgical system incorporating a dispersive return pad for monopolar and/or bipolar operations.

FIG. 8 illustrates yet another embodiment of an electrosurgical system 440 incorporating a dispersive return pad 450 attached to the electrosurgical probe 400. In this embodiment, the invention functions in the bipolar mode as described above. In addition, the system 440 may function in a monopolar mode in which a high frequency voltage difference is applied between the active electrode(s) 410, and the dispersive return pad 450. In the exemplary embodiment, the pad 450 and the probe 400 are coupled together, and are both disposable, single-use items. The pad 450 includes an electrical connector 452 that extends into handle 404 of probe 400 for direct connection to the power supply. Of course, the invention would also be operable with a standard return pad that connects directly to the power supply. In this embodiment, the power supply 460 will include a switch, e.g., a foot pedal 462, for switching between the monopolar and bipolar modes. In the bipolar mode, the return path on the power supply is coupled to return electrode 408 on probe 400, as described above. In the monopolar mode, the return path on the power supply is coupled to connector 452 of pad 450, active electrode(s) 410 are decoupled from the electrical circuit, and return electrode 408 functions as the active electrode. This allows the surgeon to switch between bipolar and monopolar modes during, or prior to, the surgical procedure. In some cases, it may be desirable to operate in the monopolar mode to provide deeper current penetration and, thus, a greater thermal heating of the tissue surrounding the return electrodes. In other cases, such as ablation of tissue, the bipolar modality may be preferable to limit the current penetration to the tissue.

In one configuration, the dispersive return pad 450 is adapted for coupling to an external surface of the patient in a region substantially close to the target region. For example, during the treatment of tissue in the head and neck, the dispersive return pad is designed and constructed for placement in or around the patient's shoulder, upper back or upper chest region. This design limits the current path through the patient's body to the head and neck area, which minimizes the damage that may be generated by unwanted current paths in the patient's body, particularly by limiting current flow through the patient's heart. The return pad is also designed to minimize the current densities at the pad, to thereby minimize patient skin burns in the region where the pad is attached.

Figure 9:
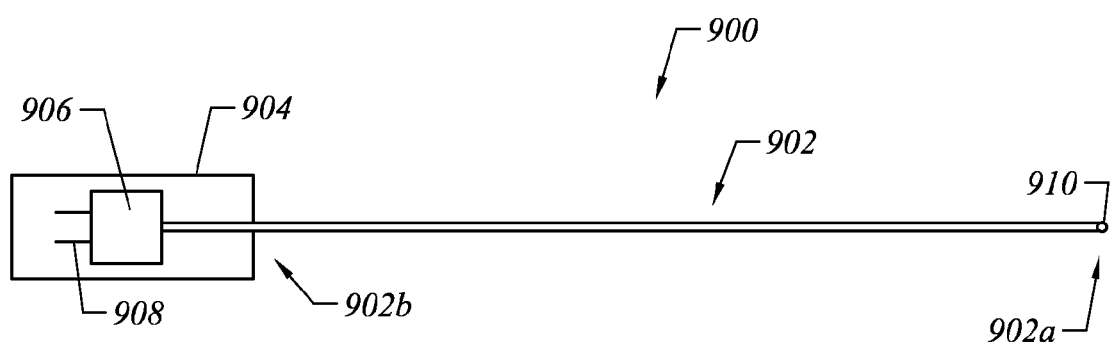
FIG. 9 is a side view of an electrosurgical probe.

FIG. 9 is a side view of an electrosurgical probe 900, according to one embodiment of the invention. Probe 900 includes a shaft 902 having a distal end portion 902a and a proximal end portion 902b. An active electrode 910 is disposed on distal end portion 902a. Although only one active electrode is shown in FIG. 9, embodiments including a plurality of active electrodes are also within the scope of the invention. Probe 900 further includes a handle 904 which houses a connection block 906 for coupling electrodes, e.g. active electrode 910, thereto. Connection block 906 includes a plurality of pins 908 adapted for coupling probe 900 to a power supply unit, e.g. power supply 28 (FIG. 2A).

Figure 10:
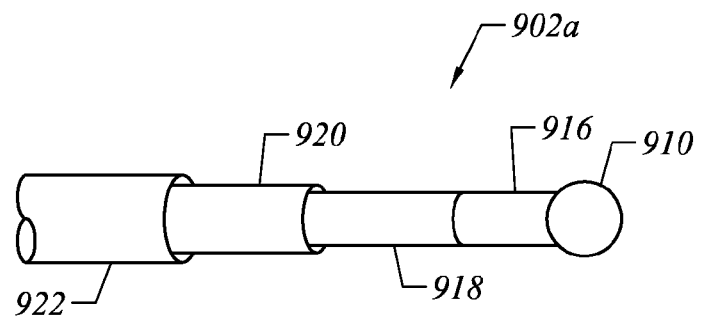
FIG. 10 is a side view of the distal end portion of the electrosurgical probe of FIG. 9.
Figure 19A:
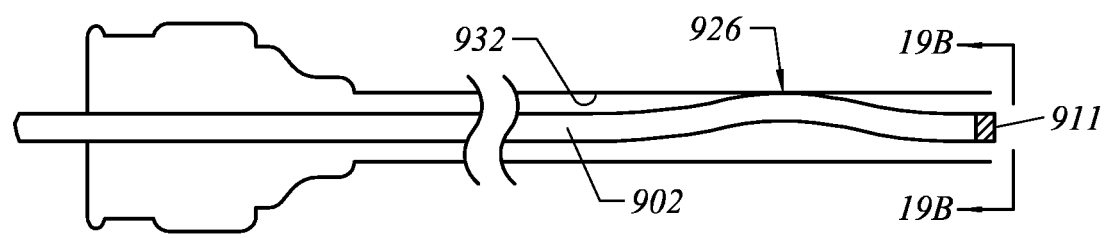
FIG. 19A, 19B show a side view and an end view, respectively, of a curved shaft of an electrosurgical probe, in relation to an introducer needle.

FIG. 10 is a side view of the distal end portion of the electrosurgical probe of FIG. 9, showing details of shaft distal end portion 902a. Distal end portion 902a includes an insulating collar or spacer 916 proximal to active electrode 910, and a return electrode 918 proximal to collar 916. A first insulating sleeve (FIG. 14) may be located beneath return electrode 918. A second insulating jacket or sleeve 920 may extend proximally from return electrode 918. Second insulating sleeve 920 serves as an electrical insulator to inhibit current flow into the adjacent tissue. In a currently preferred embodiment, probe 900 further includes a shield 922 extending proximally from second insulating sleeve 920. Shield 922 may be formed from a conductive metal such as stainless steel, and the like. Shield 922 functions to decrease the amount of leakage current passing from probe 900 to a patient or a user (e.g., surgeon). In particular, shield 922 decreases the amount of capacitive coupling between return electrode 918 and an introducer needle 928 (FIG. 19A). Typically shield 922 is coupled to an outer floating conductive layer or cable shield (not shown) of a cable, e.g. cables 22, 34 (FIG. 2A), connecting probe 900 to power supply 28. In this way, the capacitor balance of shaft 902 is disturbed. In one embodiment, shield 922 may be coated with a durable, hard compound such as titanium nitride. Such a coating has the advantage of providing reduced friction between shield 922 and introducer inner wall 932 as shaft 902 is axially translated within introducer needle 928 (e.g., FIGS. 19A, 19B).

Figure 11:
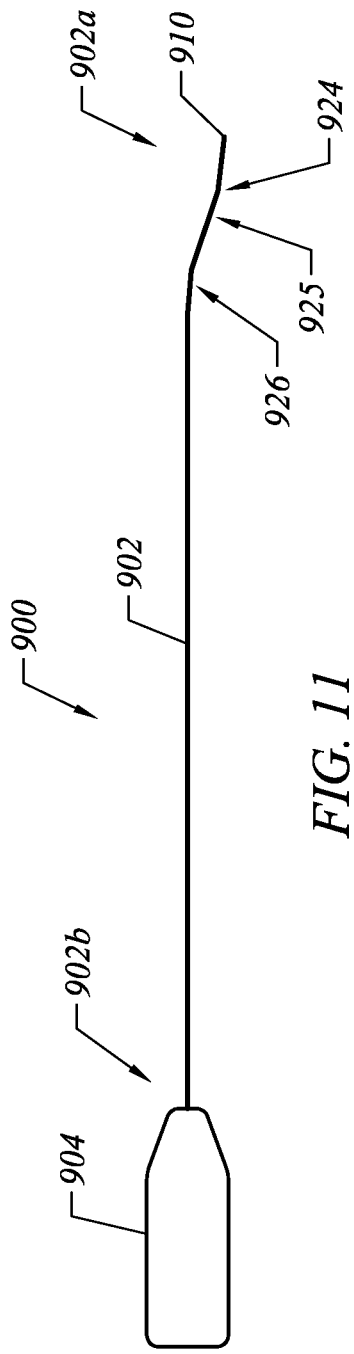
FIG. 11 is a side view of an electrosurgical probe having a curved shaft.

FIG. 11 is a side view of an electrosurgical probe 900 showing a first curve 924 and a second curve 926 located at distal end portion 902a, wherein second curve 926 is proximal to first curve 924. First curve 924 and second curve 926 may be separated by a linear (i.e. straight, or non-curved), or substantially linear, inter-curve portion 925 of shaft 902.

Figure 12:
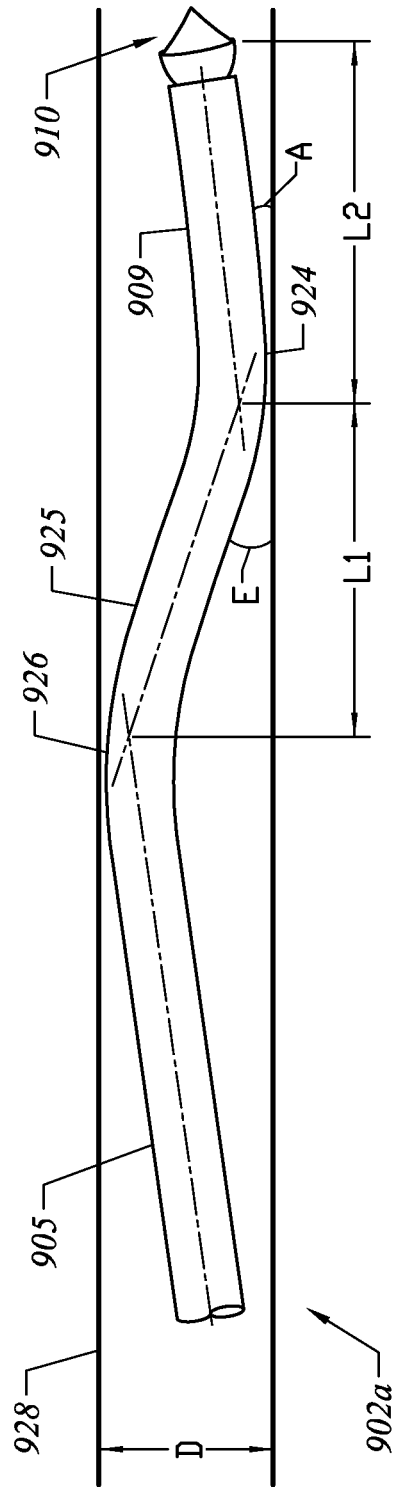
FIG. 12 is a side view of the distal end portion of the curved shaft of FIG. 11, with the shaft distal end portion within an introducer device.

FIG. 12 is a side view of shaft distal end portion 902a within a representative introducer device or needle 928 having an inner diameter D. Shaft distal end portion 902a includes first curve 924 and second curve 926 separated by inter-curve portion 925. In one embodiment, shaft distal end portion 902a includes a linear or substantially linear proximal portion 901 extending from proximal end portion 902b to second curve 926, a linear or substantially linear inter-curve portion 925 between first and second curves 924, 926, and a linear or substantially linear distal portion 909 between first curve 924 and the distal tip of shaft 902 (the distal tip is represented in FIG. 12 as an electrode head 911). When shaft distal end portion 902a is located within introducer needle 928, first curve 924 subtends a first angle ∀ to the inner surface of needle 928, and second curve 926 subtends a second angle ∃ to inner surface 932 of needle 928. (In the situation shown in FIG. 12, needle inner surface 932 is essentially parallel to the longitudinal axis of shaft proximal end portion 902b (FIG. 11).) In one embodiment, shaft distal end portion 902a is designed such that the shaft distal tip occupies a substantially central transverse location within the lumen of introducer needle 928 when shaft distal end portion 902a is translated axially with respect to introducer needle 928. Thus, as shaft distal end portion 902a is advanced through the distal opening of needle 928 (FIGS. 16B, 19A), and then retracted back into the distal opening, the shaft distal tip will always occupy a transverse location towards the center of introducer needle 928 (even though the tip may be curved or biased away from the longitudinal axis of shaft 902 and needle 928 upon its advancement past the distal opening of introducer needle 928). In one embodiment, shaft distal end portion 902a is flexible and has a configuration which requires shaft distal end portion 902a be distorted in the region of at least second curve 926 by application of a lateral force imposed by inner wall 932 of introducer needle 928 as shaft distal end portion 902a is introduced or refracted into needle 928. In one embodiment, first curve 924 and second curve 926 are in the same plane relative to the longitudinal axis of shaft 902, and first and second curves 924, 926 are in opposite directions.

The "S-curve" configuration of shaft 902 shown in FIGS. 11-C allows the distal end or tip of a device to be advanced or retracted through needle distal end 928a and within the lumen of needle 928 without the distal end or tip contacting introducer needle 928. Accordingly, this design allows a sensitive or delicate component to be located at the distal tip of a device, wherein the distal end or tip is advanced or retracted through a lumen of an introducer instrument comprising a relatively hard material (e.g., an introducer needle comprising stainless steel). This design also allows a component located at a distal end or tip of a device to be constructed from a relatively soft material, and for the component located at the distal end or tip to be passed through an introducer instrument comprising a hard material without risking damage to the component comprising a relatively soft material.

The "S-curve" design of shaft distal end portion 902a allows the distal tip (e.g., electrode head 911) to be advanced and retracted through the distal opening of needle 928 while avoiding contact between the distal tip and the edges of the distal opening of needle 928. (If, for example, shaft distal end portion 902a included only a single curve the distal tip would ordinarily come into contact with needle distal end 928a as shaft 902 is retracted into the lumen of needle 928.) In preferred embodiments, the length L2 of distal portion 909 and the angle $\forall$ between distal portion 909 and needle inner surface 932 928, when shaft distal end portion 902a is compressed within needle 928, are selected such that the distal tip is substantially in the center of the lumen of needle 928, as shown in FIG. 12. Thus, as the length L2 increases, the angle $\forall$ will decrease, and vice versa. The exact values of length L2 and angle $\forall$ will depend on the inner diameter, D of needle 928, the inner diameter, d of shaft distal end portion 902a, and the size of the shaft distal tip.

The presence of first and second curves, 924, 926 provides a pre-defined bias in shaft 902. In addition, in one embodiment shaft distal end portion 902a is designed such that at least one of first and second curves 924, 926 are compressed to some extent as shaft distal end portion 902a is retracted into the lumen of needle 928. Accordingly, the angle of at least one of curves 924, 926 may be changed when distal end portion 902a is advanced out through the distal opening of introducer needle 928, as compared with the corresponding angle when shaft distal end portion is completely retracted within introducer needle 928. For example, FIG. 27C shows shaft 902 of FIG. 12 free from introducer needle 928, wherein first and second curves 924, 926 are allowed to adopt their natural or uncompressed angles $\forall'$ and $\exists'$, respectively, wherein $\exists'$ is typically equal to or greater than $\exists$. Angle $\forall'$ may be greater than, equal to, or less than angle $\forall$. Angle $\exists'$ is subtended by inter-curve portion 925 and proximal portion 901. When shaft distal end portion 902a is unrestrained by introducer needle 928, proximal portion 901 approximates the longitudinal axis of shaft 902. Angle $\forall'$ is subtended between linear distal portion 909 and a line drawn parallel to proximal portion 901. Electrode head 911 is omitted from FIG. 27C for the sake of clarity.

The principle described above with reference to shaft 902 and introducer needle 928 may equally apply to a range of other medical devices. That is to say, the "S-curve" configuration of the invention may be included as a feature of any medical system or apparatus in which a medical instrument may be axially translated or passed within an introducer device. In particular, the principle of the "S-curve" configuration of the invention may be applied to any apparatus wherein it is desired that the distal end of the medical instrument does not contact or impinge upon the introducer device as the medical instrument is advanced from or retracted into the introducer device. The introducer device may be any apparatus through which a medical instrument is passed. Such medical systems may include, for example, a catheter, a cannula, an endoscope, and the like.

When shaft 902 is advanced distally through the needle lumen to a point where second curve 926 is located distal to needle distal end 928a, the shaft distal tip is deflected from the longitudinal axis of needle 928. The amount of this deflection is determined by the relative size of angles $\exists'$ and $\forall'$, and the relative lengths of L1 and L2. The amount of this deflection will in turn determine the size of a channel or lesion (depending on the application) formed in a tissue treated by electrode head 911 when shaft 902 is rotated circumferentially with respect to the longitudinal axis of probe 900.

As a result of the pre-defined bias in shaft 902, shaft distal end portion 902a will contact a larger volume of tissue than a linear shaft having the same dimensions. In addition, in one embodiment the pre-defined bias of shaft 902 allows the physician to guide or steer the distal tip of shaft 902 by a combination of axial movement of needle distal end 928a and the inherent curvature at shaft distal end portion 902a of probe 900.

Shaft 902 preferably has a length in the range of from about 4 to 30 cm. In one aspect of the invention, probe 900 is manufactured in a range of sizes having different lengths and/or diameters of shaft 902. A shaft of appropriate size can then be selected by the surgeon according to the body structure or tissue to be treated and the age or size of the patient. In this way, patients varying in size from small children to large adults can be accommodated. Similarly, for a patient of a given size, a shaft of appropriate size can be selected by the surgeon depending on the organ or tissue to be treated, for example, whether an intervertebral disc to be treated is in the lumbar spine or the cervical spine. For example, a shaft suitable for treatment of a disc of the cervical spine may be substantially smaller than a shaft for treatment of a lumbar disc. For treatment of a lumbar disc in an adult, shaft 902 is preferably in the range of from about 15 to 25 cm. For treatment of a cervical disc, shaft 902 is preferably in the range of from about 4 to about 15 cm.

The diameter of shaft 902 is preferably in the range of from about 0.5 to about 2.5 mm, and more preferably from about 1 to 1.5 mm. First curve 924 is characterized by a length L1, while second curve 926 is characterized by a length L2 (FIG. 12). Inter-curve portion 925 is characterized by a length L3, while shaft 902 extends distally from first curve 924 a length L4. In one embodiment, L2 is greater than L1. Length L1 may be in the range of from about 0.5 to about 5 mm, while L2 may be in the range of from about 1 to about 10 mm. Preferably, L3 and L4 are each in the range of from about 1 to 6 mm.

Figure 13:
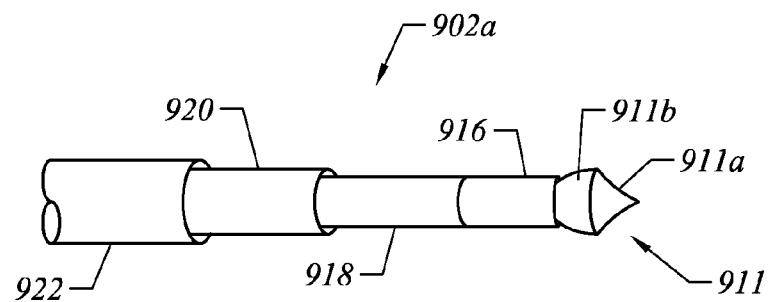
FIG. 13 is a side view of the distal end portion of an electrosurgical probe showing an active electrode having an apical spike and an equatorial cusp.

FIG. 13 is a side view of shaft distal end portion 902a of electrosurgical probe 900 showing a head 911 of active electrode 910 (the latter not shown in FIG. 13), according to one embodiment of the invention. In this embodiment, electrode head 911 includes an apical spike 911a and an equatorial cusp 911b. Electrode head 911 exhibits a number of advantages as compared with, for example, an electrosurgical probe having a blunt, globular, or substantially spherical active electrode. In particular, electrode head 911 provides a high current density at apical spike 911a and cusp 911b. In turn, high current density in the vicinity of an active electrode is advantageous in the generation of a plasma; and, as is described fully hereinabove, generation of a plasma in the vicinity of an active electrode is fundamental to ablation of tissue with minimal collateral thermal damage according to certain embodiments of the instant invention. Electrode head 911 provides an additional advantage, in that the sharp edges of cusp 911b, and more particularly of apical spike 911a, facilitate movement and guiding of head 911 into tissue during surgical procedures, as described fully hereinbelow. In contrast, an electrosurgical probe having a blunt or rounded apical electrode is more likely to follow a path of least resistance, such as a channel which was previously ablated within nucleus pulposus tissue. Although certain embodiments of the invention depict head 911 as having a single apical spike, other shapes for the apical portion of active electrode 910 are also within the scope of the invention.

Figure 14:
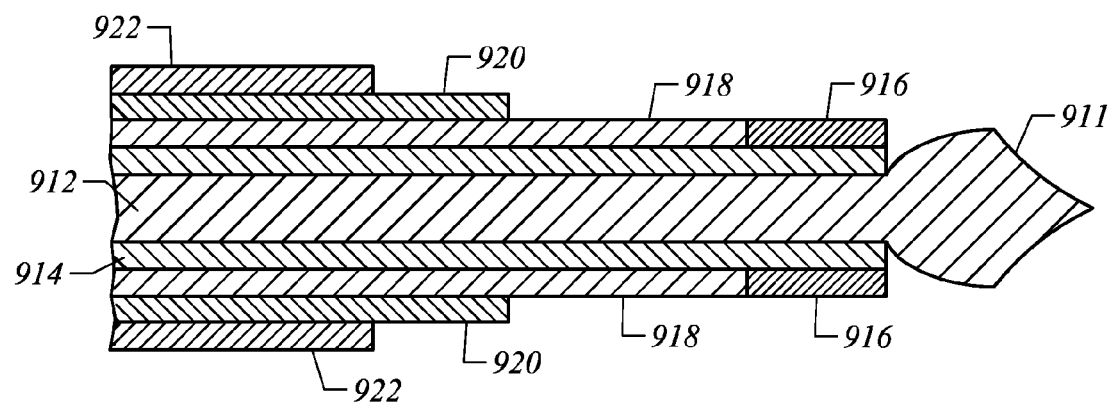
FIG. 14 is a cross-sectional view of the distal end portion of the electrosurgical probe of FIG. 13.

FIG. 14 is a longitudinal cross-sectional view of distal end portion 902a of shaft 902. Apical electrode head 911 is in communication with a filament 912. Filament 912 typically comprises an electrically conductive wire encased within a first insulating sleeve 914. First insulating sleeve 914 comprises an insulator, such as various synthetic polymeric materials. An exemplary material from which first insulating sleeve 914 may be constructed is a polyimide. First insulating sleeve 914 may extend the entire length of shaft 902 proximal to head 911. An insulating collar or spacer 916 is disposed on the distal end of first insulating sleeve 914, adjacent to electrode head 911. Collar 916 preferably comprises a material such as a glass, a ceramic, or silicone. The exposed portion of first insulating sleeve 914 (i.e., the portion proximal to collar 916) is encased within a cylindrical return electrode 918. Return electrode 918 may extend proximally the entire length of shaft 902. Return electrode 918 may comprise an electrically conductive material such as stainless steel, tungsten, platinum or its alloys, titanium or its alloys, molybdenum or its alloys, nickel or its alloys, and the like. A proximal portion of return electrode 918 is encased within a second insulating sleeve 920, so as to provide an exposed band of return electrode 918 located distal to second sleeve 920 and proximal to collar 916. Second sleeve 920 provides an insulated portion of shaft 920 which facilitates handling of probe 900 by the surgeon during a surgical procedure. A proximal portion of second sleeve 920 is encased within an electrically conductive shield 922. Second sleeve 920 and shield 922 may also extend proximally for the entire length of shaft 902.

Figure 15:
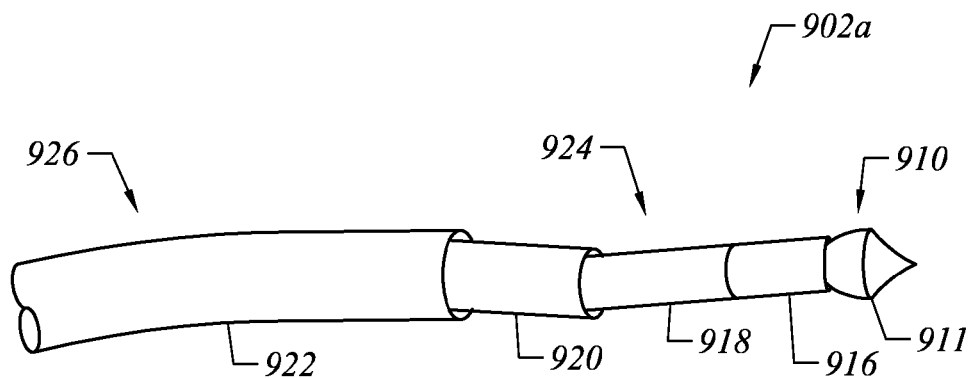
FIG. 15 is a side view of the distal end portion a shaft of an electrosurgical probe, indicating the position of a first curve and a second curve in relation to the head of the active electrode.

FIG. 15 is a side view of shaft distal end portion 902a of electrosurgical probe 900, indicating the position of first and second curves 924, 926, respectively. Probe 900 includes head 911, collar 916, return electrode 918, second insulating sleeve 920, and shield 922, generally as described with reference to FIGS. 13, 14. In the embodiment of FIG. 15, first curve 924 is located within return electrode 918, while second curve 926 is located within shield 922. However, according to various embodiments of the invention, shaft 902 may be provided in which one or more curves are present at alternative or additional locations or components of shaft 902, other than the location of first and second curves 924, 926, respectively, shown in FIG. 15.

Figure 16A:
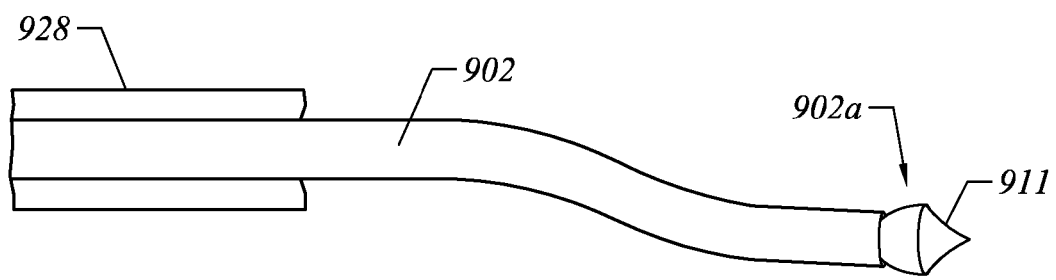
FIG. 16A shows the distal end portion of the shaft of an electrosurgical probe extended distally from an introducer needle.
Figure 16B:
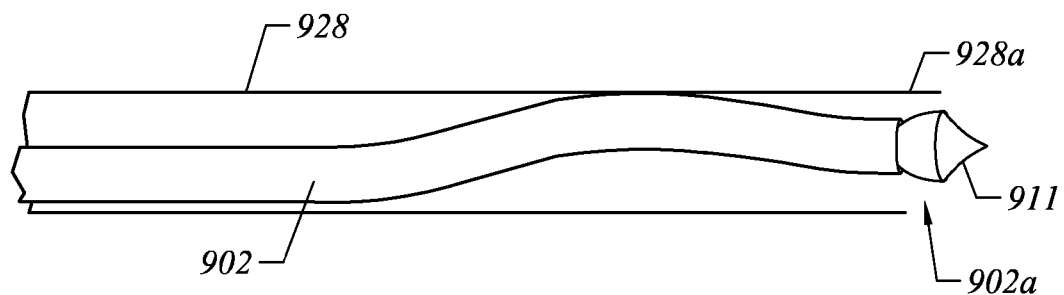
FIG. 16B illustrates the position of the active electrode in relation to the inner wall of the introducer needle upon retraction of the active electrode within the introducer needle.

FIG. 16A shows distal end portion 902a of shaft 902 extended distally from an introducer needle 928, according to one embodiment of the invention. Introducer needle 928 may be used to conveniently introduce shaft 902 into tissue, such as the nucleus pulposus of an intervertebral disc. In this embodiment, due to the curvature of shaft distal end 902a, when shaft 902 is extended distally beyond introducer needle 928, head 911 is displaced laterally from the longitudinal axis of introducer needle 928. However, as shown in FIG. 16B, as shaft 902 is retracted into introducer needle 928, head 911 assumes a substantially central transverse location within lumen 930 (see also FIG. 19B) of introducer 928. Such re-alignment of head 911 with the longitudinal axis of introducer 928 is achieved by specific design of the curvature of shaft distal end 902a, as accomplished by the instant inventors. In this manner, contact of various components of shaft distal end 902a (e.g., electrode head 911, collar 916, return electrode 918) is prevented, thereby not only facilitating extension and refraction of shaft 902 within introducer 928, but also avoiding a potential source of damage to sensitive components of shaft 902.

Figure 17A:
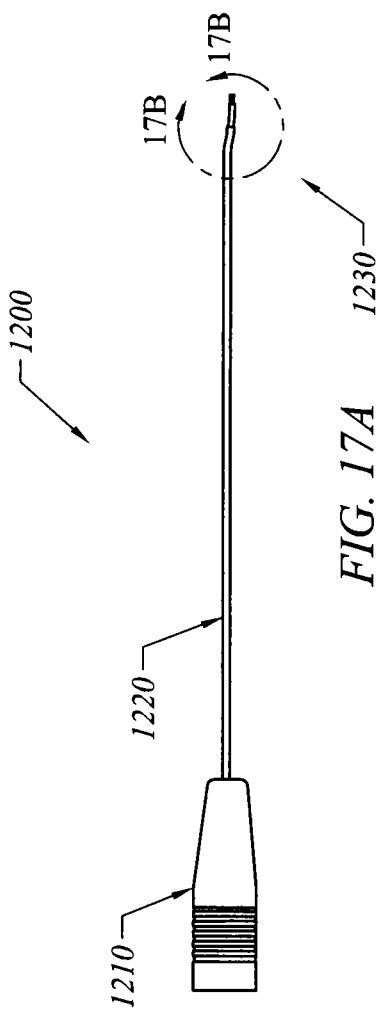
FIG. 17A shows a probe having a curved distal end and a plurality of active electrodes arranged in a bouquet.
Figure 17B:
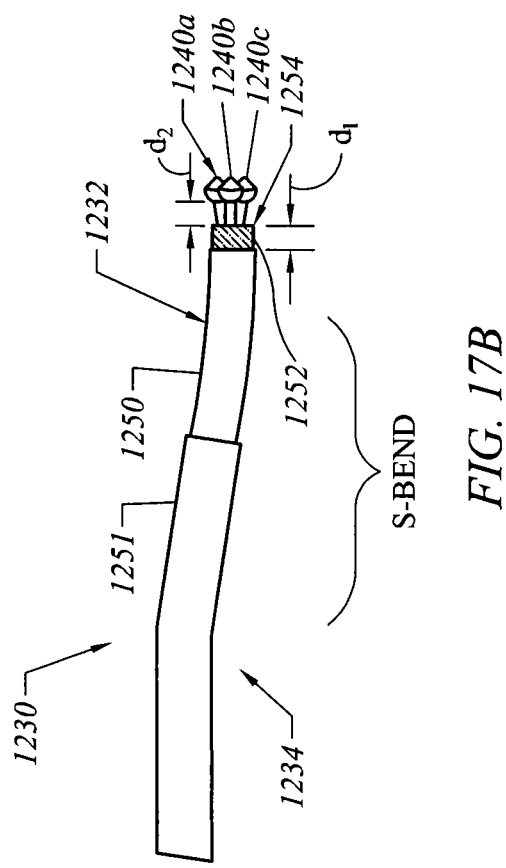
FIG. 17B shows an enlarged view of the distal end section of the probe shown in FIG. 17A.
Figure 17C:
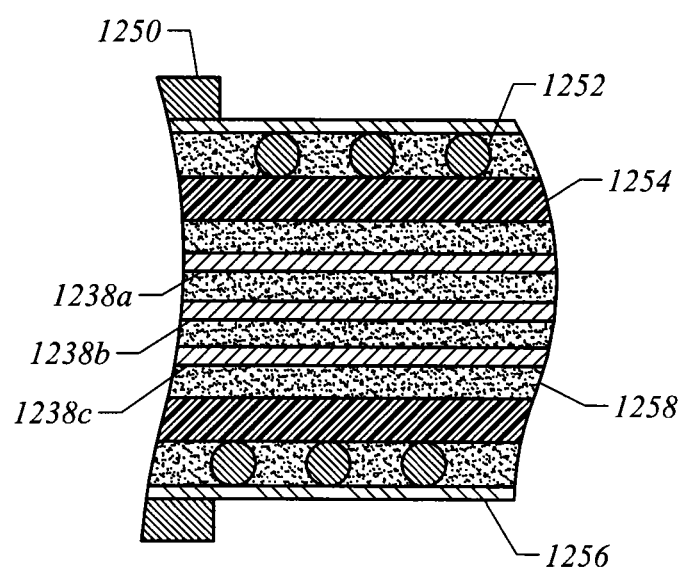
FIG. 17C shows a partial cross section of a distal section of the probe shown in FIG. 17B.

FIGS. 17A-C show another electrosurgical probe 1200 that may perform a spinal surgery as well as other types of surgery. In particular, the probe shown in FIGS. 17A-17C is intended for minimally invasive surgeries that may require relatively large volumes or cavities to be formed in a bone body such as removal of a bone tumor in a vertebral body.

Referring to FIG. 17A, the probe 1200 comprises a proximal end 1210 that is adapted to connect with a cable, an elongate shaft 1220, and a curved distal end 1230. The overall length of the probe may vary depending on the application. An exemplary length for the shaft 1220 in a spinal surgery procedure may be about 8-9 inches not including the proximal end connector 1210. The probe diameter may range from 1 to 5 mm, and in one variation ranges from 2 to 2.5 mm.

FIG. 17B shows an enlarged view of the distal end section of probe 1200 of FIG. 17A. Distal end section 1230 includes a first bend 1232 and a second bend 1234 forming an "s-curve" similar to that described in the above mentioned probes. This type of bend tends to prevent the active electrodes 1240a-c on the distal tip from contacting an introducer needle (not shown) when the active electrodes exit the introducer needle and enter the target tissue. Similarly, when the active electrodes are withdrawn into the introducer needle when the surgery is complete the s-curve tends to prevent the active electrode from contacting the introducer needle. Contact between the introducer needle and the active electrodes can have detrimental effects on the ablation energy and is thus undesirable. The angle may vary and an exemplary angle is about 9 degrees.

The distance from the second bend 1234 to the active electrode tip may vary. An exemplary distance may range from 20 to 30 mm and perhaps about 25 mm. Although the probe shown in FIG. 17A includes a particular bend, the invention is not intended to be so limited unless specifically recited so in the appended claims. Indeed, the probe may have no bend or other types of bends and curvatures.

The probe 1200 also includes a return electrode 1250 arranged proximal to the active electrodes on the shaft. The return electrode is coated with a polymeric coating 1251 proximally and includes a length of exposed metal ranging from 0.5 to 10 mm and perhaps about 5 to 7 mm. A voltage difference is applied between the active electrodes and the return electrode to ablate tissue during an application. In some cases, an electrolytically conductive fluid is delivered in the target area and contacts the return and active electrodes. As described above, the electrolytically conductive fluid is vaporized and a plasma is formed when a proper voltage differential is applied between the electrodes. The plasma-mediated ablation removes tissue quickly.

The active electrodes shown in FIG. 17B are arranged in a bouquet. The active electrodes thus spread to a degree when they are not confined by another member such as an introducer needle. This arrangement allows a larger ablation channel to be formed during an application. More tissue may be removed. The active electrodes may be shaped variously including a shape as shown in FIG. 17B. The shape shown in FIG. 17B includes an equatorial cusp and an apical tip. The shape shown in FIG. 17B is believed to quickly remove tissue without causing necrosis of collateral tissue.

Each of the plurality of active electrodes are connected to a wire conductor that extends through the shaft. The wire conductors collectively form a wire bundle and are joined to a cable (not shown) that connects the probe to an electrical source. Each of the wire conductors may be covered with a thin polymeric coating such as polyimide.

FIG. 17C shows a partial cross section of a distal section of the probe 1200. In particular, wire conductors 1238*a-c* are shown forming a wire bundle. Additionally, an inner tubular non-electrically conducting member 1254 is coaxially arranged on the exterior of the wire bundle to provide an electrical gap between the active electrodes 1240 and the return electrode 1250. The tubular member may be, for example, a silicone tube. The silicone tube may extend a distance ($d_1$) from the distal edge of the return electrode 1250. Distance $d_1$ may range from 0.25 to 2 mm and more preferably from 0.75 to 1.25 mm and perhaps about 1 mm. Also, the electrode heads may be spaced a distance ($d_2$) from the distal edge of the silicone tube. Distance $d_2$ may range from 0.25 to 2.5 mm and may be about 0.5 mm in one variation of the invention.

A securing member 1252 is arranged over the exterior of the silicone tube/wire bundle. An example of a securing member may be a metal wire that is helically wrapped around the wire bundle to prevent the active electrodes from radially expanding more than a desired amount. The metal wire may be stainless steel, titanium, molybdenum, etc. The metal wire may also have a polymeric coating such as polyimide. The thickness of the coating may vary and may be as small as about 15 microns. However, the polymeric coatings may have other thicknesses. Accordingly, the active electrodes are prevented from radially expanding more than a predetermined amount in an application (such as when the probe is inserted into tissue and is no longer radially confined to the lumen of an introducer needle). It is also to be understood, however, that a small amount of radially expansion may be desirable to form a larger ablation channel than the inner diameter of the lumen of the introducer needle.

Additionally, a redundant member 1256 may be arranged over the helically wrapped wire member. The redundant member may be, for example, heat shrink wrap tube and it may extend coaxially to cover the whole length of the inner silicone tube. An adhesive 1258 such as UV adhesive or a silicone adhesive may be added to bond all the components together.

Figure 18A:
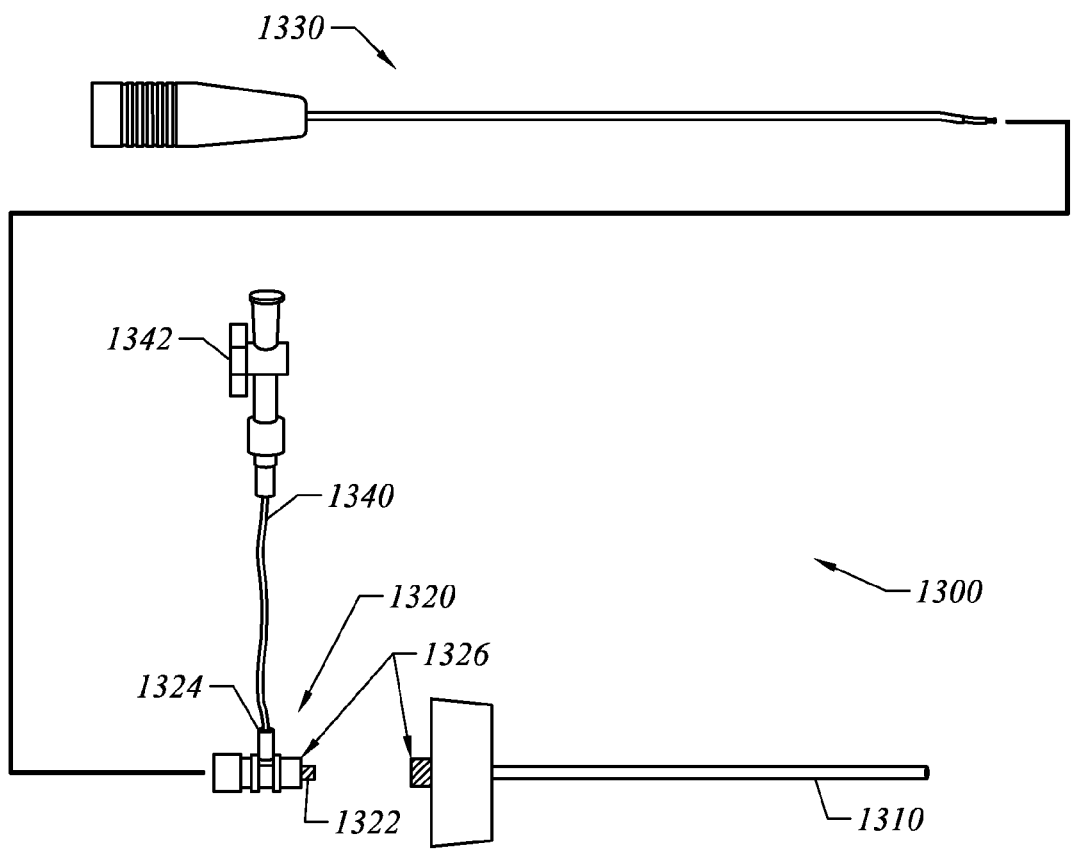
FIG. 18A shows a probe assembly in an expanded view including a probe, a fluid connector, and an introducer needle.
Figure 18B:
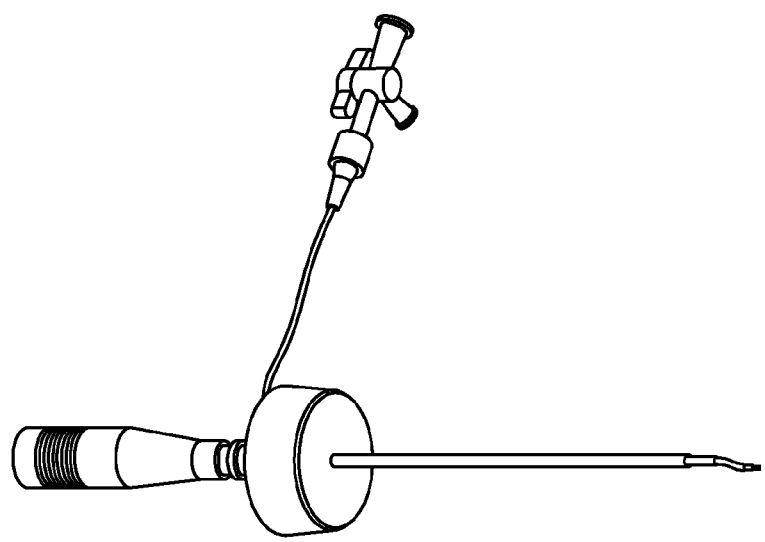
FIG. 18B shows the probe assembly of FIG. 18A assembled.

FIGS. 18A-18B show an electrosurgical assembly or kit 1300 including an introducer needle 1310, a fluid connector 1320, and an electrosurgical probe 1330 as described above in connection with FIGS. 17A-C.

The assembly may be used in a number of procedures such as the procedures described above in connection with FIGS. 1A-1H.

FIG. 18A shows an exploded view illustrating how the components are interconnected. In particular, the probe 1330 is inserted through connector 1320 and through needle 1310. The needle may be rigid and have a length suitable for the type of procedure.

The connector has an egress end 1322 that is configured to fluidly connect with a proximal end of the introducer needle. For example, connector and introducer needle may have Luer-type threads 1326. The connector further includes an ingress port 1324 for accepting fluid from a fluid source. A flexible tube 1340 may fluidly connect the fluid connector to a stopcock 1342 that is configured to receive fluid from the fluid source. Indeed, a wide variety of fluid connector assemblies may be employed to supply liquid to the introducer needle.

The introducer needle 1310 directs fluid to the target region where the active electrodes of the probe are positioned. In this manner, the active electrodes may operate in the presence of electrically conductive fluid. The probe tip may be urged distally and proximally relative to the introducer needle. An example of a fluid connector 1320 is a male TOUHY BORST with side port.

FIG. 18B shows the components described above in an assembled view.

Figure 19B:
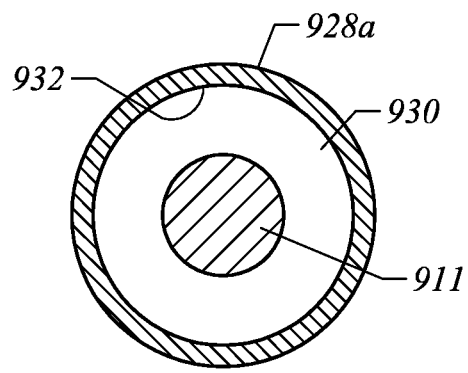

FIG. 19A shows a side view of shaft 902 in relation to an inner wall 932 of introducer needle 928 upon extension or retraction of electrode head 911 from, or within, introducer needle 928. Shaft 902 is located within introducer 928 with head 911 adjacent to introducer distal end 928*a* (FIG. 19B). Under these circumstances, curvature of shaft 902 may cause shaft distal end 902*a* to be forced into contact with introducer inner wall 932, e.g., at a location of second curve 926. Nevertheless, due to the overall curvature of shaft 902, and in particular the nature and position of first curve 924 (FIGS. 11-B), head 911 does not contact introducer distal end 928*a*.

FIG. 19B shows an end view of electrode head 911 in relation to introducer needle 928 at a point during extension or retraction of shaft 902, wherein head 911 is adjacent to introducer distal end 928*a* (FIGS. 16B, 19B). In this situation, head 911 is substantially centrally positioned within lumen 930 of introducer 928. Therefore, contact between head 911 and introducer 928 is avoided, allowing shaft distal end 902*a* to be extended and retracted repeatedly without sustaining any damage to shaft 902.

Figure 20:
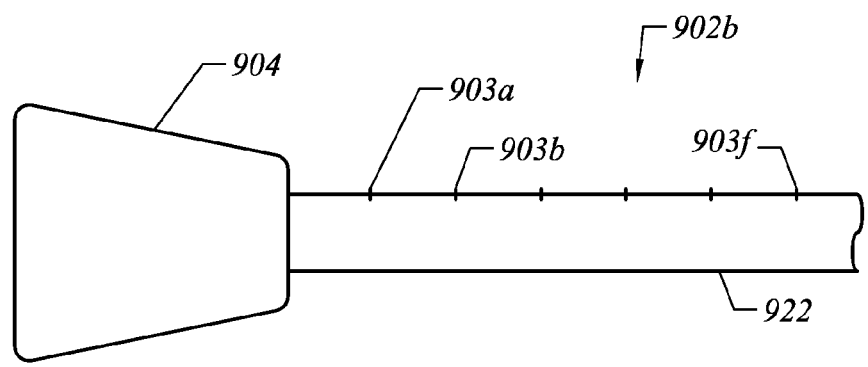
FIG. 20 shows the proximal end portion of the shaft of an electrosurgical probe, wherein the shaft includes a plurality of depth markings.

FIG. 20 shows shaft proximal end portion 902*b* of electrosurgical probe 900, wherein shaft 902 includes a plurality of depth markings 903 (shown as 903 *a-f* in FIG. 20). In other embodiments, other numbers and arrangements of depth markings 903 may be included on shaft 902. For example, in certain embodiments, depth markings may be present along the entire length of shield 922, or a single depth marking 903 may be present at shaft proximal end portion 902*b*. Depth markings serve to indicate to the surgeon the depth of penetration of shaft 902 into a patient's tissue, organ, or body, during a surgical procedure. Depth markings 903 may be formed directly in or on shield 922, and may comprise the same material as shield 922. Alternatively, depth markings 903 may be formed from a material other than that of shield 922. For example, depth markings may be formed from materials which have a different color and/or a different level of radiopacity, as compared with material of shield 922. For example, depth markings may comprise a metal, such as tungsten, gold, or platinum oxide (black), having a level of radiopacity different from that of shield 922. Such depth markings may be visualized by the surgeon during a procedure performed under fluoroscopy. In one embodiment, the length of the introducer needle and the shaft 902 are selected to limit the range of the shaft beyond the distal tip of the introducer needle.

Figure 21:
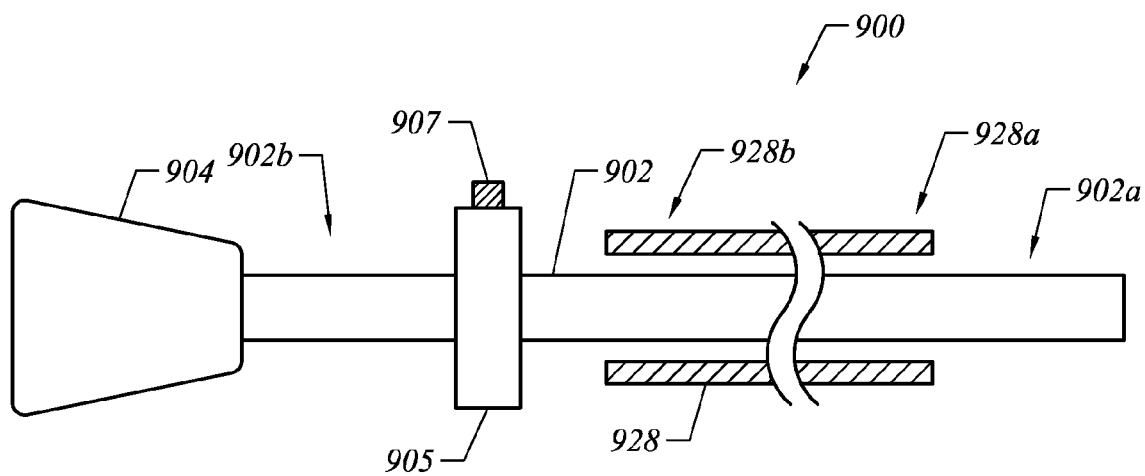
FIG. 21 shows the proximal end portion of the shaft of an electrosurgical probe, wherein the shaft includes a mechanical stop.

FIG. 21 shows a probe 900, wherein shaft 902 includes a mechanical stop 905. Preferably, mechanical stop 905 is located at shaft proximal end portion 902*b*. Mechanical stop 905 limits the distance to which shaft distal end 902*a* can be advanced through introducer 928 by making mechanical contact with a proximal end 928*b* of introducer 928. Mechanical stop 905 may be a rigid material or structure affixed to, or integral with, shaft 902. Mechanical stop 905 also serves to monitor the depth or distance of advancement of shaft distal end 902*a* through introducer 928, and the degree of penetration of distal end 902*a* into a patient's tissue, organ, or body. In one embodiment, mechanical stop 905 is movable on shaft 902, and stop 905 includes a stop adjustment unit 907 for adjusting the position of stop 905 and for locking stop 905 at a selected location on shaft 902.

Figure 22:
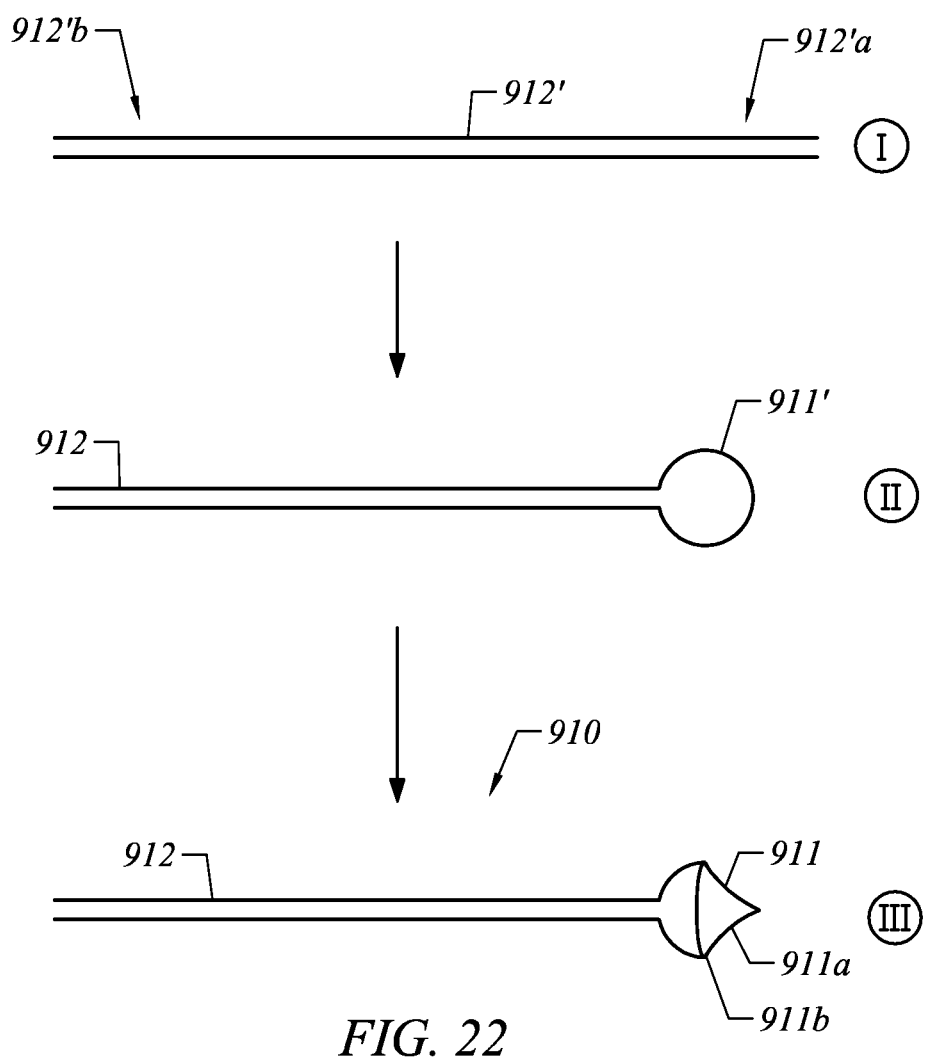
FIG. 22 illustrates stages in manufacture of an active electrode of an electrosurgical probe.

FIG. 22 illustrates stages in manufacture of an active electrode 910 of a shaft 902, according to one embodiment of the present invention. Stage 22-I shows an elongated piece of electrically conductive material 912', e.g., a metal wire, as is well known in the art. Material 912' includes a first end 912'a and a second end 912'b. Stage 22-II shows the formation of a globular structure 911' from first end 912'a, wherein globular structure 911' is attached to filament 912. Globular structure 911' may be conveniently formed by applying heat to first end 912'a. Techniques for applying heat to the end of a metal wire are well known in the art. Stage 22-III shows the formation of an electrode head 911 from globular structure 911', wherein active electrode 910 comprises head 911 and filament 912 attached to head 911. In this particular embodiment, head 911 includes an apical spike 911a and a substantially equatorial cusp 911b.

Figure 23:
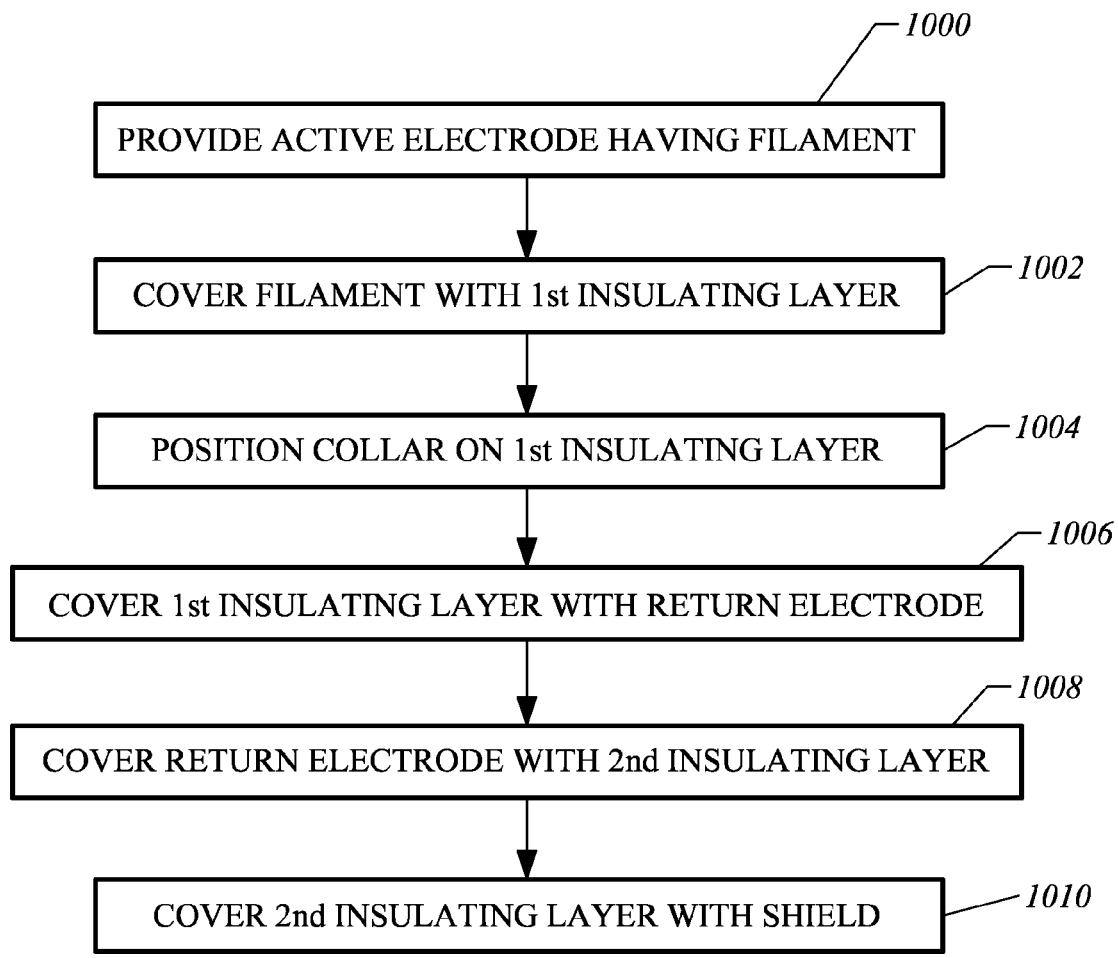
FIG. 23 schematically represents a series of steps involved in a method of making a probe shaft.

FIG. 23 schematically represents a series of steps involved in a method of making a shaft according to one embodiment of the present invention, wherein step 1000 involves providing an active electrode having a filament, the active electrode including an electrode head attached to the filament. An exemplary active electrode to be provided in step 1000 is an electrode of the type described with reference to FIG. 22. At this stage (step 1000), the filament may be trimmed to an appropriate length for subsequent coupling to a connection block (FIG. 9).

Step 1002 involves covering or encasing the filament with a first insulating sleeve of an electrically insulating material such as a synthetic polymer or plastic, e.g., a polyimide. Preferably, the first insulating sleeve extends the entire length of the shaft. Step 1004 involves positioning a collar of an electrically insulating material on the distal end of the first insulating sleeve, wherein the collar is located adjacent to the electrode head. The collar is preferably a material such as a glass, a ceramic, or silicone. Step 1006 involves placing a cylindrical return electrode over the first insulating sleeve. Preferably, the return electrode is positioned such that its distal end is contiguous with the proximal end of the collar, and the return electrode preferably extends proximally for the entire length of the shaft. The return electrode may be constructed from stainless steel or other non-corrosive, electrically conductive metal.

According to one embodiment, a metal cylindrical return electrode is pre-bent to include a curve within its distal region (i.e. the return electrode component is bent prior to assembly onto the shaft). As a result, the shaft assumes a first curve upon placing the return electrode over the first insulating sleeve, i.e. the first curve in the shaft results from the bend in the return electrode. Step 1008 involves covering a portion of the return electrode with a second insulating layer or sleeve such that a band of the return electrode is exposed distal to the distal end of the second insulating sleeve. In one embodiment, the second insulating sleeve comprises a heat-shrink plastic material which is heated prior to positioning the second insulating sleeve over the return electrode. According to one embodiment, the second insulating sleeve is initially placed over the entire length of the shaft, and thereafter the distal end of the second insulating sleeve is cut back to expose an appropriate length of the return electrode. Step 1010 involves encasing a proximal portion of the second insulating sleeve within a shield of electrically conductive material, such as a cylinder of stainless steel or other metal, as previously described herein.

Figure 24:
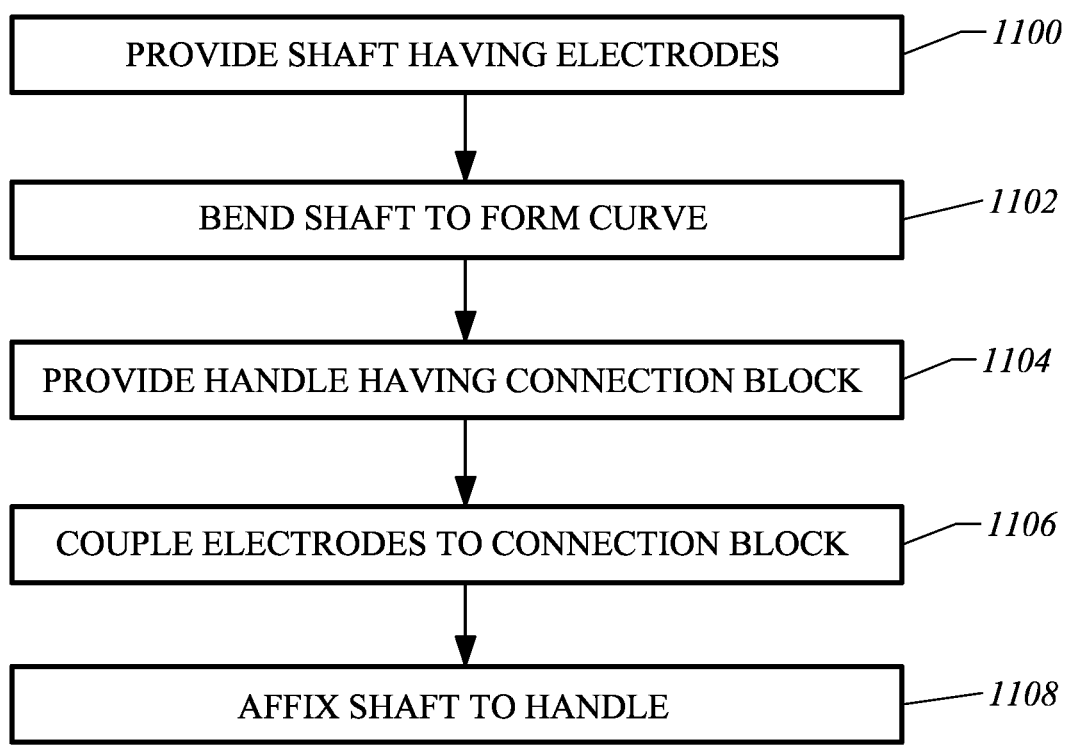
FIG. 24 schematically represents a series of steps involved in a method of making an electrosurgical probe.

FIG. 24 schematically represents a series of steps involved in a method of making an electrosurgical probe of the present invention, wherein step 1100 involves providing a shaft having at least one active electrode and at least one return electrode. An exemplary shaft to be provided in step 1100 is that prepared according to the method described hereinabove with reference to FIG. 23, i.e., the shaft includes a first curve. Step 1102 involves bending the shaft to form a second curve. Preferably, the second curve is located at the distal end portion of the shaft, but proximal to the first curve. In one embodiment, the second curve is greater than the first curve. (Features of both the first curve and second curve have been described hereinabove, e.g., with reference to FIG. 12.) Step 1104 involves providing a handle for the probe. The handle includes a connection block for electrically coupling the electrodes thereto. Step 1106 involves coupling the active and return electrodes of the shaft to the connection block. The connection block allows for convenient coupling of the electrosurgical probe to a power supply (e.g., power supply 28, FIG. 2A). Thereafter, step 1108 involves affixing the shaft to the handle.

Figure 25:
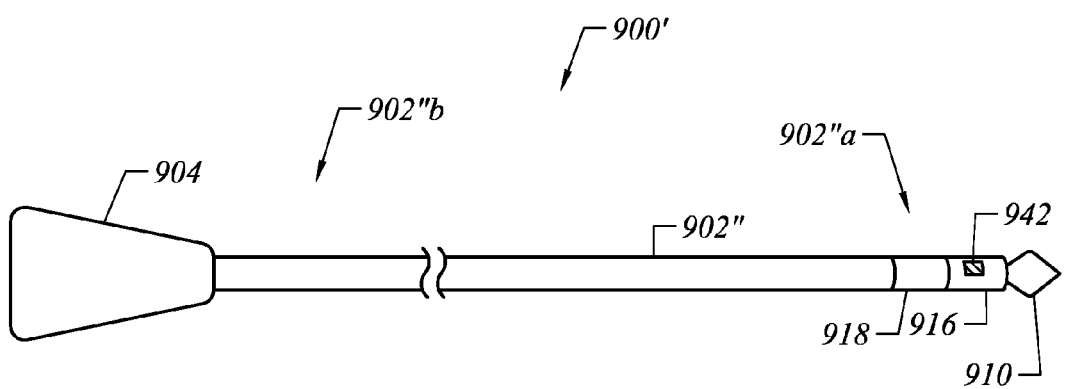
FIG. 25 shows a probe with a marker.

FIG. 25 is a side view of an electrosurgical probe 900' including shaft 902" having tracking device 942 located at distal end portion 902"a. Tracking device 942 may serve as a radiopaque marker adapted for guiding distal end portion 902"a within a bone body or disc. Shaft 902" also includes at least one active electrode 910 disposed on the distal end portion 902"a. Preferably, electrically insulating support member or collar 916 is positioned proximal of active electrode 910 to insulate active electrode 910 from at least one return electrode 918. In most embodiments, the return electrode 918 is positioned on the distal end portion of the shaft 902" and proximal of the active electrode 910. In other embodiments, however, return electrode 918 can be omitted from shaft 902", in which case at least one return electrode may be provided on ancillary device 940, or the return electrode may be positioned on the patient's body, as a dispersive pad (not shown).

Although active electrode 910 is shown in FIG. 25 as comprising a single apical electrode, other numbers, arrangements, and shapes for active electrode 910 are within the scope of the invention. For example, active electrode 910 can include a plurality of isolated electrodes in a variety of shapes. Active electrode 910 will usually have a smaller exposed surface area than return electrode 918, such that the current density is much higher at active electrode 910 than at return electrode 918. Preferably, return electrode 918 has a relatively large, smooth surfaces extending around shaft 902" in order to reduce current densities in the vicinity of return electrode 918, thereby minimizing damage to non-target tissue.

While bipolar delivery of a high frequency energy is the preferred method of debulking the nucleus pulposus, it should be appreciated that other energy sources (i.e., resistive, or the like) can be used, and the energy can be delivered with other methods (i.e., monopolar, conductive, or the like) to debulk the nucleus.

Figure 26:
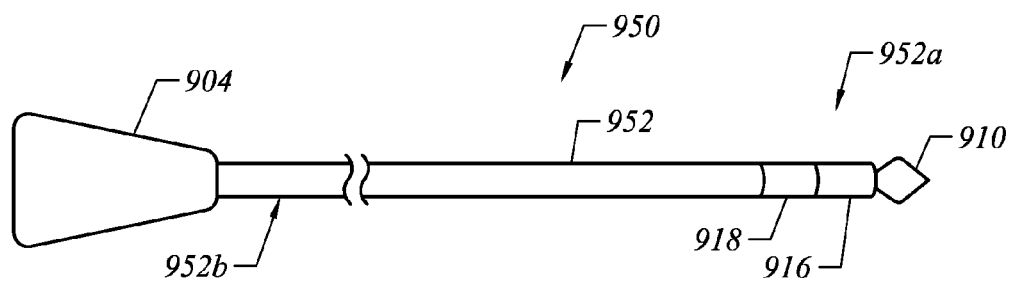
FIGS. 26-27 show a probe that may flex.
Figure 27:
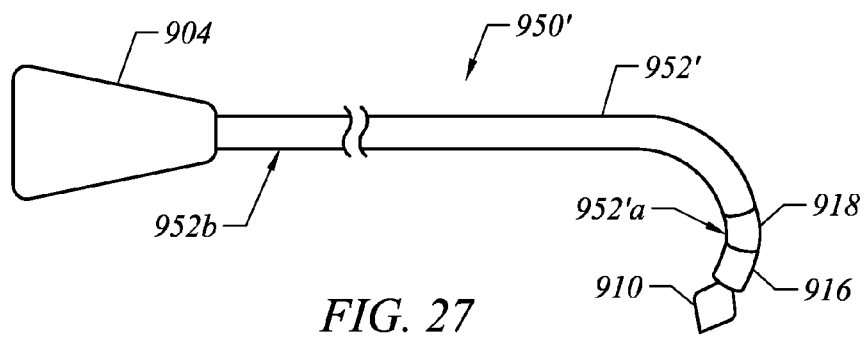

FIG. 26 shows a steerable electrosurgical probe 950 including a shaft 952, according to another embodiment of the invention. Preferably, shaft 952 is flexible and may assume a substantially linear configuration as shown. Probe 950 includes handle 904, shaft distal end 952a, active electrode 910, insulating collar 916, and return electrode 918. As can be seen in FIG. 27, under certain circumstances, e.g., upon application of a force to shaft 952 during guiding or steering probe 950 during a procedure, shaft distal end 952a can adopt a non-linear configuration, designated 952'a. The deformable nature of shaft distal end 952'a allows active electrode 910 to be guided to a specific target site within a bone body or disc.

Although the invention has been described primarily with respect to electrosurgical treatment of the spine, it is to be understood that the methods and apparatus of the invention are also applicable to the treatment of other tissues, organs, and bodily structures. For example, the principle of the "S-curve" configuration of the invention may be applied to any medical system or apparatus in which a medical instrument is passed within an introducer device, wherein it is desired that the distal end of the medical instrument does not contact or impinge upon the introducer device as the instrument is advanced from or retracted within the introducer device. The introducer device may be any apparatus through which a medical instrument is passed. Such a medical system or apparatus may include, for example, a catheter, a cannula, an endoscope, and the like. Thus, while the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. An apparatus for removing tissue within a bone body comprising:
    an elongate shaft having a distal end;
    at least two active electrodes arranged at or near said distal end;
    a wire bundle having at least two wire conductors, said wire conductors extending at least partially through said shaft and connected to said at least two active electrodes in a one to one correspondence;
    a return electrode spaced proximal to said active electrodes; and
    a helically wrapped wire member around a distal section of said wire bundle to prevent a proximal section of the at least two active electrodes from spreading apart from one another in an application while allowing a degree of radial spread of a distal section of the at least two active electrodes.

2. The apparatus of claim 1 wherein said helically wrapped wire member comprises a polymeric coated metal wire.

3. The apparatus of claim 2 further comprising a polymeric tubular member arranged concentrically with said wire bundle, said polymeric tubular member being between said wire bundle and said helically wrapped wire member.

4. The apparatus of claim 1 wherein said apparatus comprises at least two bends, each bend being between 5 and 30 degrees.

5. The apparatus of claim 1 wherein each of said at least two active electrodes has a cusp and an apical tip.

6. The apparatus of claim 5 wherein said at least two active electrodes form a bouquet arrangement.

7. The apparatus of claim 1 further comprising a fluid connector, said fluid connector comprising a fluid ingress port configured to fluidly communicate with a fluid source, and a fluid egress port configured to fluidly communicate with an introducer needle assembly, said fluid connector also adapted to axially slide along said shaft.

8. A kit comprising:
    an introducer needle for penetrating a vertebrae;
    an apparatus as recited in claim 1; and
    a high frequency controller in electrical communication with said apparatus.

9. The kit of claim 8 further comprising a fluid valve adapted to couple to a fluid source and to a proximal end of said introducer needle, and said valve further being slideable along said shaft.

10. The kit of claim 9 wherein said apparatus further comprises a suction lumen for aspirating materials from the target site.

11. The kit of claim 8 wherein the degree of radial spread of the at least two active electrodes is limited to not confine the at least two active electrodes by the introducer needle.

* * * * *